US006576445B1

(12) United States Patent
Olsen et al.

(10) Patent No.: US 6,576,445 B1
(45) Date of Patent: Jun. 10, 2003

(54) CHEMOKINE α-4

(75) Inventors: Henrik S. Olsen, Gaithersburg, MD (US); Steven M. Ruben, Olney, MD (US); Zhi-Zhen Zeng, Gaithersburg, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 51 days.

(21) Appl. No.: 09/630,709

(22) Filed: Aug. 1, 2000

Related U.S. Application Data

(63) Continuation of application No. 08/927,440, filed on Sep. 11, 1997, now abandoned.

(60) Provisional application No. 60/026,180, filed on Sep. 12, 1996.

(51) Int. Cl.[7] ......................... C12P 21/06; A61K 38/00; C07K 2/00; C07K 4/00; C07K 5/00

(52) U.S. Cl. ...................... 435/69.5; 435/325; 530/300; 530/350; 530/386; 530/387.1; 530/387.3; 530/387.9; 530/388.1; 530/388.15; 530/388.23; 530/389.1; 530/389.2; 530/391.1; 530/391.3; 530/391.5; 530/391.7; 530/391.9

(58) Field of Search ................................ 530/300, 350, 530/386, 387.1, 387.3, 387.9, 388.1, 388.15, 388.23, 389.1, 389.2, 391.1, 391.3, 391.5, 391.7, 391.9; 435/325, 69.5

(56) References Cited

U.S. PATENT DOCUMENTS

| | | |
|---|---|---|
| 5,556,757 A | 9/1996 | Alystyne et al. |
| 5,556,767 A | 9/1996 | Rosen et al. |
| 5,700,924 A | 12/1997 | Braxton et al. |
| 5,707,829 A | 1/1998 | Jacobs et al. |
| 5,929,210 A | 7/1999 | Braxton et al. |
| 5,955,284 A | 9/1999 | Braxton et al. |

FOREIGN PATENT DOCUMENTS

| | | |
|---|---|---|
| EP | 088 7409 | 5/1998 |
| WO | 94/04670 | 3/1994 |
| WO | 96/24668 | 8/1996 |
| WO | 97/07198 | 2/1997 |
| WO | 98/32858 | 7/1998 |
| WO | 99/13082 | 3/1999 |

OTHER PUBLICATIONS

Harlow and Lane. Antibodies, A laboratory manual. Cold Spring Harlbor Laboratory. 1988, pp. 14, 149, 196, 210, 217, 240, 241, 321–324, 340, 342, 343 and 353.*

Genbank Accession No.: AAB17374 (Oct. 23, 1996).

Genbank Accession No.: AA361853 (Apr. 21, 1997).

Geneseq Accession No.: W90124 (Dec. 30, 1998).

Rani, M. R. S. et al., The Journal of Biol. Chem., vol. 271(37):22878–22884 (1996).

Adams, M. R. et al., Nature, vol. 377(Supp. 28):3–174 (1995).

Van Regenmortel, M. H. V. et al., Ann Biol. Clin., vol. 51:39–41 (1993).

Van Regenmortel, M. H. V. et al, Immunology Letters, vol. 17:95–108 (1988).

Jameson B. A. et al., CAMBIOS, vol. 4(1):181–186 (1988).

Strieter et al. "The Role of C–X–C Chemokines in Regulation of Angiogenesis", (1996), Koch, A.E. & Strieter, R.M. Eds., R.G. Landes Co. London, pp. 195–209.

R and D Systems, 1995 Catalog, pp. 80–85.

Tanh and al. Therapeutic Immunol. 1:229–246 (1994).

Howard et al., TIBTECH 14:46–51 (1996).

Luster et al., Letts. to Nature 315:672–676 (1985).

Geneseq Accession No. AAV86134, Agostino et al., "New polynucleotides encoding human secreted proteins—derived from e.g. human blood, kidney, foetal lung, placenta, testes, brain, ovary, pituitary, retina and colon cDNA libraries," Apr. 27, 1999.

* cited by examiner

*Primary Examiner*—Anthony C. Caputa
*Assistant Examiner*—Alana M. Harris
(74) *Attorney, Agent, or Firm*—Human Genome Sciences, Inc.

(57) ABSTRACT

The present invention relates to a novel CKα-4 protein which is a member of the CXC chemokine family. In particular, isolated nucleic acid molecules are provided encoding the human CKα-4 protein. CKα-4 polypeptides are also provided as are vectors, host cells and recombinant methods for producing the same. The invention further relates to screening methods for identifying agonists and antagonists of CKα-4 activity. Also provided are diagnostic methods for detecting immune system-related disorders and therapeutic methods for treating immune system-related disorders.

27 Claims, 5 Drawing Sheets

Figure 1

```
      AGCCAAGAAGAGCAGCAAAGCTGAAGTAGCAGCAGCAGCACCAGCAGCAACAGCAAAAAA
  1   ---------+---------+---------+---------+---------+---------+   60

      CAAACATGAGTGTGAAGGGCATGGCTATAGCCTTGGCTGTGATATTGTGTGCTACAGTTG
 61   ---------+---------+---------+---------+---------+---------+   120
           MetSerValLysGlyMetAlaIleAlaLeuAlaValIleLeuCysAlaThrValV
            M  S  V  K  G  M  A  I  A  L  A  V  I  L  C  A  T  V  V   19

      TTCAAGGCTTCCCCATGTTCAAAAGAGGACGCTGTCTTTGCATAGGCCCTGGGGTAAAAG
121   ---------+---------+---------+---------+---------+---------+   180
      alGlnGlyPheProMetPheLysArgGlyArgCysLeuCysIleGlyProGlyValLysA
 20    Q  G  F  P  M  F  K  R  G  R  C  L  C  I  G  P  G  V  K  A     39

      CAGTGAAAGTGGCAGATATTGAGAAAGCCTCCATAATGTACCCAAGTAACAACTGTGACA
181   ---------+---------+---------+---------+---------+---------+   240
      laValLysValAlaAspIleGluLysAlaSerIleMetTyrProSerAsnAsnCysAspL
 40    V  K  V  A  D  I  E  K  A  S  I  M  Y  P  S  N  N  C  D  K     59

      AAATAGAAGTGATTATTACCCTGAAAGAAAATAAAGGACAACGATGCCTAAATCCCAAAT
241   ---------+---------+---------+---------+---------+---------+   300
      ysIleGluValIleIleThrLeuLysGluAsnLysGlyGlnArgCysLeuAsnProLysS
 60    I  E  V  I  I  T  L  K  E  N  K  G  Q  R  C  L  N  P  K  S     79

      CGAAGCAAGCAAGGCTTATAATCAAAAAAGTTGAAAGAAAGAATTTTTAAAAATATCAAA
301   ---------+---------+---------+---------+---------+---------+   360
      erLysGlnAlaArgLeuIleIleLysLysValGluArgLysAsnPheEnd
 80    K  Q  A  R  L  I  I  K  K  V  E  R  K  N  F  *                 94

      ACATATGAAGTCCTGGAAAAGAGCATCTGAAAAACCTAGAACAAGTTTAACTGTGACTAC
361   ---------+---------+---------+---------+---------+---------+   420

      TGAAATGACAAGAATTCTACAGTAGGAAACTGAGACTTTTCTATGGTTTTGTGACTTTCA
421   ---------+---------+---------+---------+---------+---------+   480

      ACTTTTGTACAGTTATGTGAAGGATGAAAGGTGGGTGAAAGGACCAAAAACAGAAATACA
481   ---------+---------+---------+---------+---------+---------+   540

      GTCTTCCTGAATGAATGACAATCAGAATTCCACTGCCCAAAGGAGTCCAACAATTAAATG
541   ---------+---------+---------+---------+---------+---------+   600

      GATTTCTAGGAAAAGCTACCTTAAGAAAAGGGCTGGTTACCATCGGAGTTTACAAAGTGC
601   ---------+---------+---------+---------+---------+---------+   660

      TTTCACGTTCTTACTTGTTGCATTAT
661   ---------+---------+------   686
```

Figure 2

```
   MSVKGMAIALAVILCATVVQGFPMFKRGRCLCIGPGVKAVKVADIEKASIMYPSNNCDKI 245
   M+    + I    + L  + +QG P+ +   RC CI     + V    +EK  I+  S  C ++
 1 MNQTAILICCLIFLTLSGIQGVPLSRTVRCTCISISNQPVNPRSLEKLEIIPASQFCPRV 60

   EVIITLKENKGQRCLNPKSKQARLIIKKVERK
   E+I T+K+    +RCLNP+SK  + ++K V ++
61 EIIATMKKKGEKRCLNPESKAIKNLLKAVSKE 92
```

Figure 4a

```
  1 CAAAGCTGAA GTAGCAGCAA CAGCACCAGC AGCAACAGCA AAAAACAAAC
 51 ATGAGTGTGA AGGGCATGGC TATAGCCTTG GCTGTGATAT TGTGTGCTAC
101 AGTTGTTCAA GGTATGCAGT AATTTTNATT TCTCAACCTA TAAGTTCCTN
151 TTCTAATGTT TCAAATGTCT TTTCTTCCAC TTTTATCCTA AAAGACATGA
201 TAAAGTTTTA TTTAATCTCA CAGATTAGAA GTTACTACAG CTTTAGCACA
251 GAAATGGTGG NCATGTTTAA GATACTAGAG ATGATTATTG AANCTAGAAA
301 TTATGGACTT CATGGAATTT TTNGGATTTG GCTAGAATTA TCTGGCAAAA
351 GNCTTTTAGG CAACCAGTTT TAAATGT
```

Figure 4b

```
       .         .         .         .
 16 CAAAGCTGAAGTAGCAGCAGCACCAGCAGCAACAGCAAAAAACAAAC 65
    ||||||||||||||||||| ||||||||||||||||||||||||||||||
  1 CAAAGCTGAAGTAGCAGCAACAGCACCAGCAGCAACAGCAAAAAACAAAC 50

            .         .         .         .         .
 66 ATGAGTGTGAAGGGCATGGCTATAGCCTTGGCTGTGATATTGTGTGCTAC 115
    ||||||||||||||||||||||||||||||||||||||||||||||||||
 51 ATGAGTGTGAAGGGCATGGCTATAGCCTTGGCTGTGATATTGTGTGCTAC 100

            .
116 AGTTGTTCAAGG 127
    ||||||||||||
101 AGTTGTTCAAGG 112
```

Figure 5a

```
  1 ACGATGCCTA AATCCCAAAT CGAAGCAAGC AAGGCTTATA ATCAAAAAAG
 51 TTGAAAGAAA GANTTTTTAA AAAATATCAA AACATATGAN GTCCTGGAAA
101 AGGGCATCTG AAAAACCTAG AACAAGTTTA ACTGTGACTA CTGAAATGAC
151 AAGAATTCTA CAGTAGGAAA CTGAGACTTT TCTATGGTTT TNTGACTTTC
201 AACTTTTGTA CAGTTATGTG AAGGATGAAA GGTGGGTGAA AGGACCAAAA
251 ACAGAAATAC AGTCTTCCTG AATGATTGAC AATCCAGANT TCCACTGCCC
301 AAAGG
```

Figure 5b

```
281 ACGATGCCTAAATCCCAAATCGAAGCAAGCAAGGCTTATAATCAAAAAAG 330
    ||||||||||||||||||||||||||||||||||||||||||||||||||
  1 ACGATGCCTAAATCCCAAATCGAAGCAAGCAAGGCTTATAATCAAAAAAG 50
               .         .         .         .         .
331 TTGAAAGAAAGAATTTTT.AAAAAATATCAAAACATATGAAGTCCTGGAAA 379
    |||||||||||:||||| |||||||||||||||||||:||||||||||
 51 TTGAAAGAAAGANTTTTTAAAAAAATATCAAAACATATGANGTCCTGGAAA 100
               .         .         .         .         .
380 AGAGCATCTGAAAAACCTAGAACAAGTTTAACTGTGACTACTGAAATGAC 429
    || |||||||||||||||||||||||||||||||||||||||||||||||
101 AGGGCATCTGAAAAACCTAGAACAAGTTTAACTGTGACTACTGAAATGAC 150
               .         .         .         .         .
430 AAGAATTCTACAGTAGGAAACTGAGACTTTTCTATGGTTTTGTGACTTTC 479
    |||||||||||||||||||||||||||||||||||||||||:||||||||
151 AAGAATTCTACAGTAGGAAACTGAGACTTTTCTATGGTTTTNTGACTTTC 200
               .         .         .         .         .
480 AACTTTTGTACAGTTATGTGAAGGATGAAAGGTGGGTGAAAGGACCAAAA 529
    ||||||||||||||||||||||||||||||||||||||||||||||||||
201 AACTTTTGTACAGTTATGTGAAGGATGAAAGGTGGGTGAAAGGACCAAAA 250
               .         .         .         .         .
530 ACAGAAATACAGTCTTCCTGAATGAATGACAAT.CAGAATTCCACTGCCC 578
    ||||||||||||||||||||||||| ||||||| ||||:|||||||||||
251 ACAGAAATACAGTCTTCCTGAATGATTGACAATCCAGANTTCCACTGCCC 300

579 AAAGG 583
    |||||
301 AAAGG 305
```

CHEMOKINE α-4

This application is a continuation of and claims priority under 35 U.S.C §120, to U.S. patent application Ser. No. 08/927,440, filed Sep. 11, 1997, abandoned which claims priority under 35 U.S.C §119(e) to U.S. Provisional Patent Application Serial No: 60/026,180, filed Sep. 12, 1996, all herein incorporated by reference in their entirety.

FIELD OF THE INVENTION

The present invention relates to a novel chemokine. More specifically, isolated nucleic acid molecules are provided encoding a human Chemokine Alpha-4, hereinafter referred to as "CKα-4". CKα-4 polypeptides are also provided, as are vectors, host cells and recombinant methods for producing the same. The invention further relates to screening methods for identifying agonists and antagonists of CKα-4 activity. Also provided are diagnostic methods for detecting immune system-related disorders and therapeutic methods for treating immune system-related disorders.

BACKGROUND OF THE INVENTION

The ability to control the migration and "trafficking" of various cell types is controlled by a subset of factors, or proteins, among which chemokines are an example. Chemokines, also referred to as intercrine cytokines, are a subfamily of structurally and functionally related chemotactic cytokines. These molecules are 8–12 kDa in size. In general, chemokines exhibit 20% to 75% homology at the amino acid level and are characterized by four conserved cysteine residues that form two disulfide bonds. Based on the arrangement of the first two cysteine residues, chemokines have been classified into two subfamilies, alpha and beta. In the alpha subfamnily, the first two cysteines are separated by one amino acid and hence are referred to as the "C—X—C" subfamily. In the beta subfamily, the two cysteines are in an adjacent position and are, therefore, referred to as the "C—C" subfamily. Thus far, over a dozen different members of this family have been identified in humans.

The intercrine cytokines exhibit a wide variety of functions. A hallmark feature is their ability to elicit chemotactic migration of distinct cell types, including monocytes, neutrophils, T lymphocytes, basophils and fibroblasts. Many chemokines have proinflammatory activity and are involved in multiple steps during an inflammatory reaction. These activities include stimulation of histamine release, lysosomal enzyme and leukotriene release, increased adherence of target immune cells to endothelial cells, enhanced binding of complement proteins, induced expression of granulocyte adhesion molecules and complement receptors, and respiratory burst. In addition to their involvement in inflammation, certain chemokines have been shown to exhibit other activities. For example, macrophage inflammatory protein 1 (MIP-1) is able to suppress hematopoietic stem cell proliferation, platelet factor-4 (PF-4) is a potent inhibitor of endothelial cell growth, interleukin-8 (L-8) promotes proliferation of keratinocytes, and GRO is an autocrine growth factor for melanoma cells.

In light of the diverse biological activities, it is not surprising that chemokines have been implicated in a number of physiological and disease conditions, including lymphocyte trafficking, wound healing, hematopoietic regulation and immunological disorders such as allergy, asthma and arthritis.

Members of the "C—C" subfamily exert their effects on the following cells: eosinophils which destroy parasites to lessen parasitic infection and cause chronic inflammation in the airways of the respiratory system; macrophages which suppress tumor formation in vertebrates; and basophils which release histamine which plays a role in allergic inflammation. However, members of one subfamily may exert an effect on cells which are normally responsive to the other branch of chemokines and, therefore, no precise role can be attached to the members of the branches.

While members of the C—C subfamily act predominantly on mononuclear cells and members of the C—X—C subfamily act predominantly on neutrophils a distinct chemoattractant property cannot be assigned to a chemokine based on this guideline. Some chemokines from one subfamily show characteristics of the other.

The polypeptide of the present invention has the conserved cysteine residues of the "C—X—C" region, and have amino acid sequence homology to known chemokines.

Clearly, there is a need for factors that regulate the migration of distinct cell types and their roles in dysfunction and disease. There is a need, therefore, for identification and characterization of such factors that regulate the migration of cells, particularly cells of the immune system, and which can play a role in preventing, ameliorating or correcting dysfunctions or diseases.

SUMMARY OF THE INVENTION

The present invention provides isolated nucleic acid molecules comprising a polynucleotide encoding the CKα-4 polypeptide having the amino acid sequence shown in FIG. 1 (SEQ ID NO:2) or the amino acid sequence encoded by the cDNA clone deposited as ATCC Deposit Number 97692 on Aug. 27, 1996. The nucleotide sequence determined by sequencing the deposited CKα-4 clone, which is shown in FIG. 1 (SEQ ID NO:1), contains an open reading frame encoding a polypeptide of 94 amino acid residues, including an initiation codon at positions 66–68, with a leader sequence of about 18 amino acid residues, and a predicted molecular weight of about 10 kDa. The amino acid sequence of the predicted mature CKα-4 protein is shown in FIG. 1, amino acid residues 19–94 (also residues 19–94 in SEQ ID NO:2).

Thus, one aspect of the invention provides an isolated nucleic acid molecule comprising a polynucleotide having a nucleotide sequence selected from the group consisting of: (a) a nucleotide sequence encoding the CKα-4 polypeptide having the complete amino acid sequence in FIG. 1 (SEQ ID NO:2); (b) a nucleotide sequence encoding the complete CKα-4 polypeptide having the amino acid sequence shown in FIG. 1 excepting the N-terminal methionine (i.e., residues 2 to 94 in SEQ ID NO:2); (c) a nucleotide sequence encoding the predicted mature CKα-4 polypeptide having the amino acid sequence at positions 19–94 in FIG. 1 (SEQ ID NO:2); (d) a nucleotide sequence encoding the CKα-4 polypeptide having the complete amino acid sequence encoded by the cDNA clone contained in ATCC Deposit No. 97692; (e) a nucleotide sequence encoding the mature CKα-4 polypeptide having the amino acid sequence encoded by the cDNA clone contained in ATCC Deposit No. 97692; and (f) a nucleotide sequence complementary to any of the nucleotide sequences in (a), (b), (c), (d) or (e) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), (d), (e) or (f), above, or a polynucleotide which hybridizes under stringent hybridization conditions to a polynucleotide in (a), (b), (c), (d), (e) or (f), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a CKα-4 polypeptide having an amino acid sequence in (a), (b), (c), (d) or (e), above.

The present invention also relates to recombinant vectors, which include the isolated nucleic acid molecules of the present invention, and to host cells containing the recombinant vectors, as well as to methods of making such vectors and host cells and for using them for production of CKα-4 polypeptides or peptides by recombinant techniques.

The invention further provides an isolated CKα-4 polypeptide having an amino acid sequence selected from the group consisting of: (a) the amino acid sequence of the CKα-4 polypeptide having the complete 94 amino acid sequence, including the leader sequence shown in FIG. 1 (SEQ ID NO:2); (b) the amino acid sequence of the CKα-4 polypeptide shown in FIG. 1 excepting the N-terminal methionine (i.e., residues 2 to 94 shown in SEQ ID NO:2) (c) the amino acid sequence of the predicted mature CKα-4 polypeptide (without the leader) having the amino acid sequence at positions 19–94 in FIG. 1 (SEQ ID NO:2); (d) the amino acid sequence of the CKα-4 polypeptide having the complete amino acid sequence, including the leader, encoded by the cDNA clone contained in ATCC Deposit No. 97692; and (e) the amino acid sequence of the mature CKα-4 polypeptide having the amino acid sequence encoded by the cDNA clone contained in ATCC Deposit No.97692. The polypeptides of the present invention also include polypeptides having an amino acid sequence with at least 90% similarity, and more preferably at least 95% similarity to those described in (a), (b), (c), (d) or (e) above, as well as polypeptides having an amino acid sequence at least 80% identical, more preferably at least 90% identical, and still more preferably 95%, 96%, 97%, 98% or 99% identical to those above.

An additional embodiment of this aspect of the invention relates to a peptide or polypeptide which has the amino acid sequence of an epitope-bearing portion of a CKα-4 polypeptide having an amino acid sequence described in (a), (b), (c), (d) or (e), above. Peptides or polypeptides having the amino acid sequence of an epitope-bearing portion of a CKα-4 polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention. In another embodiment, the invention provides an isolated antibody that binds specifically to a CKα-4 polypeptide having an amino acid sequence described in (a), (b), (c), (d) or (e) above.

The invention further provides methods for isolating antibodies that bind specifically to a CKα-4 polypeptide having an amino acid sequence as described herein. Such antibodies are useful diagnostically or therapeutically as described below.

The present invention also provides a screening method for identifying compounds capable of enhancing or inhibiting a cellular response induced by the CKα-4, which involves contacting cells which express the CKα-4 with the candidate compound, assaying a cellular response, and comparing the cellular response to a standard cellular response, the standard being assayed when contact is made in the absence of the candidate compound; whereby, an increased cellular response over the standard indicates that the compound is an agonist and a decreased cellular response over the standard indicates that the compound is an antagonist.

In another aspect, a screening assay for agonists and antagonists is provided which involves determining the effect a candidate compound has on CKα-4 binding to the CKα-4 receptor. In particular, the method involves contacting the CKα-4 receptor with a CKα-4 polypeptide and a candidate compound and determining whether CKα-4 polypeptide binding to the CKα-4 receptor is increased or decreased due to the presence of the candidate compound.

The present inventor has discovered that CKα-4 is expressed in g-interferon induced epithelial tissue. For a number of immune system-related disorders, significantly higher or lower levels of CKα-4 gene expression may be detected in certain tissues (e.g., cancerous and wounded tissues) or bodily fluids (e.g., serum, plasma, urine, synovial fluid or spinal fluid) taken from an individual having such a disorder, relative to a "standard" CKα-4 gene expression level, i.e., the CKα-4 expression level in healthy tissue from an individual not having the immune system disorder. Thus, the invention provides a diagnostic method useful during diagnosis of immune system disorders, which involves: (a) assaying the CKα-4 gene expression level in cells or body fluid of an individual; (b) comparing the CKα-4 gene expression level with a standard CKα-4 gene expression level, whereby an increase or decrease in the assayed CKα-4 gene expression level compared to the standard expression level is indicative of an immune system disorder.

An additional aspect of the invention is related to a method for treating an individual in need of an increased level of CKα-4 activity in the body comprising administering to such an individual a composition comprising a therapeutically effective amount of an isolated CKα-4 polypeptide of the invention or an agonist thereof.

A still further aspect of the invention is related to a method for treating an individual in need of a decreased level of CKα-4 activity in the body comprising, administering to such an individual a composition comprising a therapeutically effective amount of an CKα-4 antagonist. Preferred antagonists for use in the present invention are CKα-4-specific antibodies and CKα-4 ELR mutants.

BRIEF DESCRIPTION OF THE FIGURES

FIG. 1 shows the nucleotide (SEQ ID NO:1) and deduced amino acid (SEQ ID NO:2) sequences of CKα-4. The protein has a leader sequence of about 18 amino acid residues and a deduced molecular weight of about 10 kDa. The amino acid sequence of the predicted mature CKα-4 protein is also shown as in residues 19–94 in FIG. 1 (SEQ ID NO:2).

FIG. 2 shows the regions of identity and similarity between the amino acid sequences of the CKα-4 protein and human mRNA for gamma-interferon inducible early response gene product (SEQ ID NO:3).

FIG. 4 shows the relationship between the deposited cDNA clone and a related cDNA clone of the invention (HLTBR66).

FIG. 4*a* shows the nucleotide sequence determined from this related clone called "HLTBR66R" (shown in the Sequence Listing as SEQ ID NO:9), and FIG. 4*b* shows the alignment of the HLTBR66R nucleotide sequence (lower line) with the nucleotide sequence determined from the deposited cDNA clone (SEQ ID NO:1) (upper line) determined by the computer program Bestfit (Wisconsin Sequence Analysis Package, Version 8 for Unix, Genetics Computer Group, University Research Park, 575 Science Drive, Madison, Wis. 53711) using the default parameters.

FIG. 5 shows the relationship between the deposited cDNA clone and a related cDNA clone of the invention (HRTAN26).

FIG. 5*a* shows the nucleotide sequence determined from this related clone called "HRTAN26R" (shown in the Sequence Listing as SEQ ID NO:10), and FIG. 5*b* shows the alignment (using Bestfit) of the HRTAN26R nucleotide sequence (lower line) with the nucleotide sequence determined from the deposited cDNA clone (SEQ ID NO:1) (upper line).

DETAILED DESCRIPTION

Figure 3:
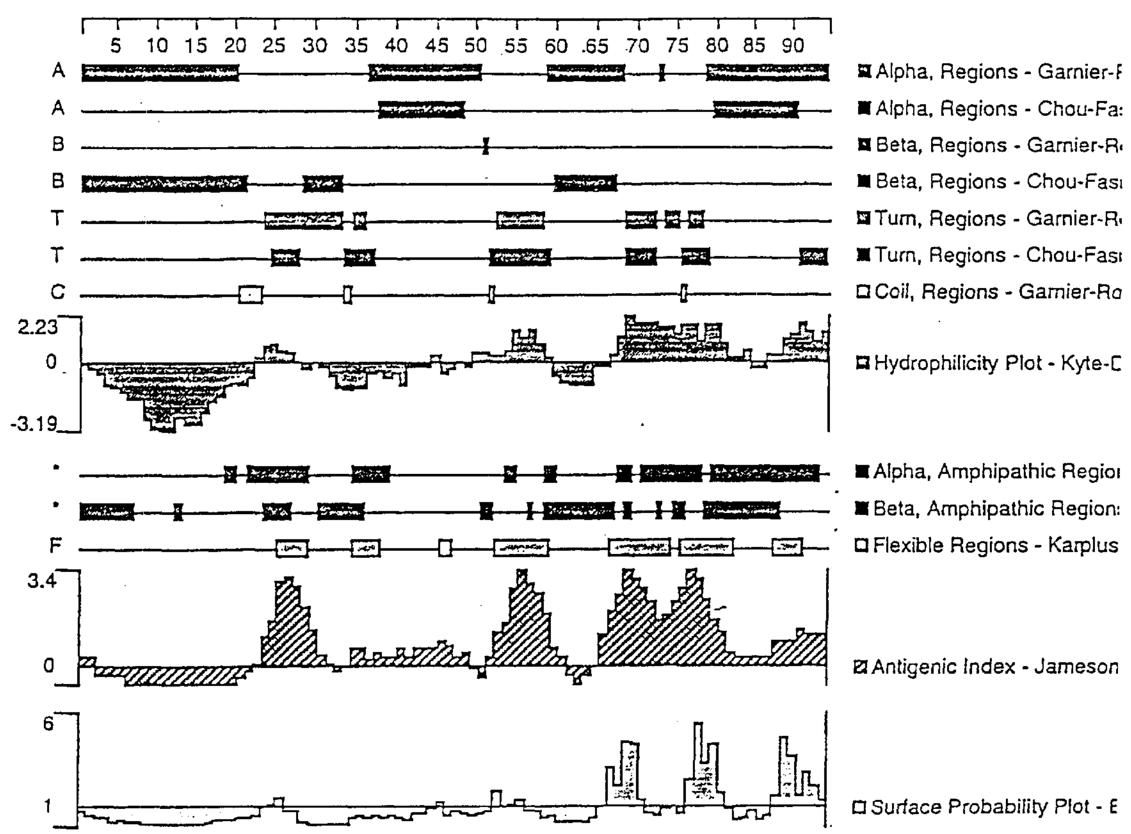
FIG. 3 shows an analysis of the CKα-4 amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues Pro 23-Cys 32; Pro 35-Ser 49; Tyr 52-Val 62; and Leu 66-Phe 94 in FIG. 1 correspond to the shown highly antigenic regions of the CKα-4 protein.

The present invention provides isolated nucleic acid molecules comprising a polynucleotide encoding a CKα-4 polypeptide having the amino acid sequence shown in FIG. 1 (SEQ ID NO:2), which was determined by sequencing a cloned cDNA. The CKα-4 protein of the present invention shares sequence homology with human mRNA for gamma-interferon inducible early response gene product ("gIP-10") (FIG. 2) (SEQ ID NO:3). gIP-10 is thought to be an important mediator of inflammation and wound healing (Luster et al., *Nature*, 315:672–676 (1985)). The homology between gIP-10 and CKα-4 suggests that CKα-4 may also be involved in the inflammatory response. Of the known alpha family chemokines, ten contain an ELR motif (IL-8, ENA-78, GCP2, GRO-a, GRO-β, GRO-g, PBP, CTAP-III, β-TG, NAP-2) and three lack the ELR motif (IP-10, PF4 and MIG). CKα-4 lacks the ELR motif immediately preceding the first cysteine residue. It has been clearly shown that this ELR motif is required for the neutrophil and endothelial cell chemotactic activity as well as the angiogenic activity of IL-8 (Strieter et al., *J. Biol. Chem.*, 270:27348–27357 (1995)). In addition, it has been shown that the ELR-CXC chemokines have in vitro and in vivo angiogenic activity, whereas the CXC chemokines lacking the ELR motif are actually angiostatic (Strieter et al., supra; Angiolillo et al., *J. Exp. Med.*, 182:155–162 (1995); and Koch et al., *Science*, 258:1798–1801 (1992)). In terms of a possible role of such factors in tumor angiogenesis, Smith et al., *J. Exp. Med.*, 179:1409–1415 (1994), has reported increased IL-8 levels in bronchogeneic carcinoma tumor tissues which appear to be produced from the tumor cells. The nucleotide sequence shown in FIG. 1 (SEQ ID NO:1) was obtained by sequencing the HAICL46 clone which was deposited on Aug. 27, 1996 at the American Type Culture Collection 10801 University Boulevard, Manassas, Va., 20110-2209, and given accesssion number 97692. The deposited clone is contained in the pBluescript SK(−) plasmid (Stratagene, La Jolla, Calif.).

Nucleic Acid Molecules

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxyribonucleotide A, G or C of SEQ ID NO:1 has been replaced by the corresponding ribonucleotide A, G or C, and each deoxyribonucleotide T has been replaced by a ribonucleotide U.

Using the information provided herein, such as the nucleotide sequence in FIG. 1, a nucleic acid molecule of the present invention encoding a CKα-4 polypeptide may be obtained using standard cloning and screening procedures, such as those for cloning cDNAs using mRNA as starting material. Illustrative of the invention, the nucleic acid molecule described in FIG. 1 (SEQ ID NO:1) was discovered in a cDNA library derived from TNFa and INFg induced human epithelial tissue. The gene was also identified in cDNA libraries from the following tissues: brain frontal cortex and human T-cell lymphoma. The determined nucleotide sequence of the CKα-4 cDNA of FIG. 1 (SEQ ID NO:1) contains an open reading frame encoding a protein of 94 amino acid residues, with an initiation codon at positions 66–68 of the nucleotide sequence in FIG. 1 (SEQ ID NO:1), a predicted leader sequence of about 18 amino acid residues, and a deduced molecular weight of about 10 kDa. The amino acid sequence of the predicted mature CKα-4 is shown in FIG. 1 (SEQ ID NO:2) from amino acid residue 19 to residue 94. The CKα-4 protein shown in FIG. 1 (SEQ ID NO:2) is about 32% identical to human mRNA for human gamma-interferon inducible early response gene product (gIP-10) (FIG. 2). Luster et al., *Nature*, 315:672–676 (1985).

More particularly, the present invention also provides the mature form(s) of the CKα-4 protein. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature CKα-4 polypeptide having the amino acid sequence encoded by the cDNA clone contained in the host identified as ATCC Deposit No. 97692. By the mature CKα-4 polypeptide having the amino acid sequence encoded by the cDNA clone in ATCC Deposit No. 97692 is meant the mature form(s) of the CKα-4 protein produced by expression in a mammalian cell (e.g., COS cells, as described below) of the complete open reading frame encoded by the human DNA sequence of the clone contained in the deposit.

In addition, methods for predicting whether a protein has a secretory leader as well as the cleavage point for that leader sequence are available because it is known that much of the cleavage specificity for a secretory protein resides in certain amino acid residues within the signal sequence and the N-terminus of the mature protein, particularly residues immediately surrounding the cleavage site. For instance, the method of McGeoch (Virus Res. 3:271–286 (1985)) uses the information from a short N-terminal charged region and a subsequent uncharged region of the complete (uncleaved) protein. The method of von Heinje (Nucleic Acids Res. 14:4683–4690 (1986)) uses the information from the residues surrounding the cleavage site, typically residues −13 to +2 where +1 indicates the amino terminus of the mature protein. The accuracy of predicting the cleavage points of known mammalian secretory proteins for each of these methods is in the range of 75–80% (von Heinje, supra). However, the two methods do not always produce the same predicted cleavage point(s) for any given protein.

In the present case, the predicted amino acid sequence of the complete CKα-4 polypeptide was analyzed by a computer program "PSORT", available from Dr. Kenta Nakai of the Institute for Chemical Research, Kyoto University (see K. Nakai and M. Kanehisa, *Genomics* 14:897–911 (1992)), which is an expert system for predicting the cellular location of a protein based on the amino acid sequence. As part of this computational prediction of localization, the methods of McGeoch and von Heinje are incorporated. The analysis by the PSORT program predicted no cleavage site within the complete amino acid sequence shown in SEQ ID NO:2. Therefore, the complete amino acid sequence was further analyzed by visual inspection, applying a simple form of the −1, −3 rule of von Heinje (von Heinje, 1986, supra. Thus, the leader sequence for the CKα-4 protein is predicted to consist of amino acid residues 1–18 of SEQ ID NO:2, while the predicted mature protein consists of residues 19–94 of SEQ ID NO:2.

As one of ordinary skill wold appreciate from the above discussions, due to the possibilities of sequencing errors as well as the variability of cleavage sites in different known proteins, the predicted mature CKα-4 polypeptide encoded by the deposited cDNA is expected to consist of about 76 amino acids (presumably residues 19–94 of SEQ ID NO:2), but may consist of any number of amino acids in the range of about 65 to about 81 amino acids; and the actual leader sequence(s) of this protein is expected to be 18 amino acids (presumably residues 1–18 of SEQ ID NO:2, but may consist of any number of amino acids in the range of about 16 to about 22 amino acids.

In addition, it is known in the art that for many proteins, including the mature form(s) of a secreted protein, that one or more amino acids may be deleted from the N-terminus without substantial loss of biological function (CKα-4 activity). In the present case, since the protein of the invention is a chemokine, deletions of N-terminal amino acids up to the first cysteine may retain some biological activity such as receptor binding and modulation of target cell activities. However, polypeptides having further deletions including the first cysteine residue would not be expected to retain such biological activities because it is known that the first cysteine after the predicted leader cleavage site in chemokines is required to form a disulfide bridge, thereby providing structural stability which is needed for receptor binding and signal transduction. However, even if deletion of one or more amino acids from the N-terminus of a protein results in modification of loss of one or more biological functions of the protein, other biological activities may still be retained. Thus, the ability of the shortened protein to induce and/or binding to antibodies which recognize the complete or mature protein generally will be retained when less than the majority of the residues of the complete or mature protein are removed from the N-terminus. Whether a particular polypeptide lacking N-terminal residues of a complete protein retains such immunologic activities can readily be determined by routine methods described herein and otherwise known in the art.

Accordingly, the present invention further provides polypeptides having one or more residues from the amino terminus of the amino acid sequence of the CKα-4 in SEQ ID NO:2, up to the first cysteine residue from the amino terminus after the predicted leader cleavage site, and polynucleotides encoding such polypeptides. In particular, the present invention provides polypeptides having the amino acid sequence of residues n-29 of the amino acid sequence in SEQ ID NO:2, where n is any integer in the specified range and residue 29 is the position of the first cysteine residue from the N-terminus of the complete polypeptide, after the predicted leader cleavage site, as shown in the amino acid sequence in SEQ ID NO:2. More in particular, the invention provides polypeptides having the amino acid sequence of residues 2–94, 3–94, 4–94, 5–94, 6–94, 7–94, 8–94, 9–94, 10–94, 11–94, 12–94, 13–94, 14–94, 15–94, 16–94, 18–94, 19–94, 20–94, 21–94, 22–94, 23–94, 24–94, 25–94, 26–94, 27–94, 28–94 and 29–94 of SEQ ID NO:2. Polynucleotides encoding these polypeptides also are provided.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) with an initiation codon at positions 66–68 of the nucleotide sequence shown in FIG. 1 (SEQ ID NO:1); DNA molecules comprising the coding sequence for the predicted mature CKα-4 protein shown in FIG. 1 (last 76 amino acids) (SEQ ID NO:2); and DNA molecules which comprise a sequence substantially different from those described above but which, due to the degeneracy of the genetic code, still encode the CKα-4 protein. Of course, the genetic code is well known in the art. Thus, it would be routine for one skilled in the art to generate the degenerate variants described above.

In another aspect, the invention provides isolated nucleic acid molecules encoding the CKα-4 polypeptide having an amino acid sequence encoded by the cDNA clone contained in the plasmid deposited as ATCC Deposit No. 97692 on Aug. 27, 1996. Preferably, this nucleic acid molecule will encode the mature polypeptide encoded by the above-described deposited cDNA clone. The invention further provides an isolated nucleic acid molecule having the nucleotide sequence shown in FIG. 1 (SEQ ID NO:1) or the nucleotide sequence of the CKα-4 cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the CKα-4 gene in human tissue, for instance, by Northern blot analysis.

The present invention is further directed to nucleic acid molecules encoding portions of the nucleotide sequences described herein as well as to fragments of the isolated nucleic acid molecules described herein. In particular, the invention provides a polynucleotide having a nucleotide sequence representing the portion of SEQ ID NO:1 selected from the group consisting of positions 1–390, 66–347, 69–347, 120–347, 129–338, 138–329, 147–320, 157–311, 166–302, 166–293 and 166–286 of SEQ ID NO:1. In addition, the invention provides nucleic acid molecules having related nucleotide sequences determined from the following related cDNA clones: clone HLTBR66 gave rise to sequence HLTBR66R shown in FIG. 4 (SEQ ID NO:9), and clone HRTAN26 gave rise to sequence HRTAN26R shown in FIG. 5 (SEQ ID NO:10). More generally, by a fragment of an isolated nucleic acid molecule having the nucleotide sequence of the deposited cDNA or the nucleotide sequence shown in FIG. 1 (SEQ ID NO:1) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–300 nt in length are also useful according to the present invention as are fragments corresponding to most, if not all, of the nucleotide sequence of the deposited cDNA or as shown in FIG. 1 (SEQ ID NO:1). By a fragment at least 20 nt in length, for example, is intended fragments which include 20 or more contiguous bases from the nucleotide sequence of the deposited cDNA or the nucleotide sequence as shown in FIG. 1 (SEQ ID NO:1). Since the gene has been deposited and the nucleotide sequence shown in FIG. 1 (SEQ ID NO:1) is provided, generating such DNA fragments would be routine to the skilled artisan. For example, restriction endonuclease cleavage or shearing by sonication could easily be used to generate fragments of various sizes. Alternatively, such fragments could be generated synthetically.

Preferred nucleic acid fragments of the present invention include nucleic acid molecules encoding epitope-bearing portions of the CKα-4 protein. In particular, such nucleic acid fragments of the present invention include nucleic acid molecules encoding: a polypeptide comprising amino acid residues from about Pro 23 to about Cys 32 in FIG. 1 (SEQ ID NO:2); a polypeptide comprising amino acid residues from about Pro 35 to about Ser 49 in FIG. 1 (SEQ ID NO:2); a polypeptide comprising amino acid residues from about Tyr 52 to about Val 62 in FIG. 1 (SEQ ID NO:2); and a polypeptide comprising amino acid residues from about Leu 66 to about Phe 94 in FIG. 1 (SEQ ID NO:2). The inventor has determined that the above polypeptide fragments are antigenic regions of the CKα-4 protein. Methods for determining other such epitope-bearing portions of the CKα-4 protein are described in detail below.

As described above CKα-4 lacks an ELR motif. By making a specific mutation in CKα-4 to include an ELR motif in the position where such a motif is typically found in related chemokines, CKα-4 will act as an antagonist, thus possessing angiogenic activity. Accordingly, polypeptides of the present invention include CKα-4 ELR mutants. Such CKα-4 ELR mutants are comprised of the full-length or mature CKα-4 polypeptide except that residues E-L-R are present in each sequence at positions 27–29 on the CKα-4 amino acid sequence shown in FIG. 1 (SEQ D NO:2). Also forming part of the present invention are isolated polynucleotides comprising nucleic acid sequences which encode said CKα-4 mutants.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit No. 97692. By "stringent hybridization conditions" is intended overnight incubation at 42° C. in a solution comprising: 50% formamide, 5×SSC (750 mM NaCl, 15mM trisodium citrate), 50 mM sodium phosphate (pH 7.6), 5×Denhardt's solution, 10% dextran sulfate, and 20 g/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

Of course, polynucleotides hybridizing to a larger portion of the reference polynucleotide (e.g., the deposited cDNA clone), for instance, a portion 50–300 nt in length, or even to the entire length of the reference polynucleotide, are also useful as probes according to the present invention, as are polynucleotides corresponding to most, if not all, of the nucleotide sequence of the deposited cDNA or the nucleotide sequence as shown in FIG. 1 (SEQ ID NO:1). By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIG. 1 (SEQ ID NO:1)). As indicated, such portions are useful diagnostically either as a probe according to conventional DNA hybridization techniques or as primers for amplification of a target sequence by the polymerase chain reaction (PCR), as described, for instance, in *Molecular Cloning, A Laboratory Manutal*, 2nd. edition, Sambrook, J., Fritsch, E. F. and Maniatis, T., eds., Cold Spring Harbor Laboratory Press, Cold Spring Harbor, N.Y. (1989), the entire disclosure of which is hereby incorporated herein by reference.

Since a CKα-4 cDNA clone has been deposited and its determined nucleotide sequence is provided in FIG. 1 (SEQ ID NO:1), generating polynucleotides which hybridize to a portion of the CKα-4 cDNA molecule would be routine to the skilled artisan. For example, restriction endonuclease cleavage or shearing by sonication of the CKα-4 cDNA clone could easily be used to generate DNA portions of various sizes which are polynucleotides that hybridize to a portion of the CKα-4 cDNA molecule. Alternatively, the hybridizing polynucleotides of the present invention could be generated synthetically according to known techniques. Of course, a polynucleotide which hybridizes only to a poly A sequence (such as the 3' terminal poly(A) tract of the CKα-4 cDNA shown in FIG. 1 (SEQ ID NO:1)), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a CKα-4 polypeptide may include, but are not limited to those encoding the amino acid sequence of the mature polypeptide, by itself; the coding sequence for the mature polypeptide and additional sequences, such as those encoding the about 18 amino acid leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., Proc. Natl. Acad. Sci. USA 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., Cell 37: 767 (1984). As discussed below, other such fusion proteins include the CKα-4 fused to immunoglobulin at the N- or C-terminus.

The present invention further relates to variants of the nucleic acid molecules of the present invention, which encode portions, analogs or derivatives of the CKα-4 protein. Variants may occur naturally, such as a natural allelic variant. By an "allelic variant" is intended one of several alternate forms of a gene occupying a given locus on a chromosome of an organism. Genes II, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the CKα-4 protein or portions thereof. Also especially preferred in this regard are conservative substitutions. Most highly preferred are nucleic acid molecules encoding the predicted mature protein having the amino acid sequence shown in FIG. 1 (SEQ ID NO:2) or the mature CKα-4 amino acid sequence encoded by the deposited cDNA clone.

Further embodiments of the invention include isolated nucleic acid molecules comprising a polynucleotide having a nucleotide sequence at least 90% identical, and more preferably at least 95%, 96%, 97%, 98% or 99% identical to (a) a nucleotide sequence encoding the full-length CKα-4 polypeptide having the complete amino acid sequence in FIG. 1 (SEQ ID NO:2), including the predicted leader sequence; (b) a nucleotide sequence encoding the full-length CKα-4 polypeptide having the complete amino acid sequence in FIG. 1 excepting the N-terminal methionine (i.e., residues 2–94 shown in SEQ ID NO:2); (c) a nucleotide sequence encoding the predicted mature CKα-4 polypeptide (full-length polypeptide with the leader removed) having the amino acid sequence at positions 19–94 in FIG. 1 (SEQ ID NO:2); (d) a nucleotide sequence encoding the full-length CKα-4 polypeptide having the complete amino acid sequence including the leader encoded by the cDNA clone contained in ATCC Deposit No. 97692; (e) a nucleotide sequence encoding the mature CKα-4 polypeptide having the amino acid sequence encoded by the cDNA clone contained in ATCC Deposit No.97692; or (f) a nucleotide sequence complementary to any of the nucleotide sequences in (a), (b), (c), (d) or (e).

By a polynucleotide having a nucleotide sequence at least, for example, 95% "identical" to a reference nucleotide sequence encoding a CKα-4 polypeptide is intended that the nucleotide sequence of the polynucleotide is identical to the reference sequence except that the polynucleotide sequence may include up to five point mutations per each 100 nucleotides of the reference nucleotide sequence encoding the CKα-4 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIG. 1 or to the nucleotide sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96%, 97%, 98% or 99% identical to the nucleic acid sequence shown in FIG. 1 (SEQ ID NO:1) or to the nucleic acid sequence of the deposited cDNA, irrespective of whether they encode a polypeptide having CKα-4 activity. This is because even where a particular nucleic acid molecule does not encode a polypeptide having CKα-4 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having CKα-4 activity include, inter alia, (1) isolating the CKα-4 gene or allelic variants thereof in a cDNA library; (2) in situ hybridization (e.g., "FISH") to metaphase chromosomal spreads to provide precise chromosomal location of the CKα-4 gene, as described in Verma et al., Human Chromosomes: A Manual of Basic Techniques, Pergamon Press, New York (1988); and Northern Blot analysis for detecting CKα-4 mRNA expression in specific tissues.

Preferred, however, are nucleic acid molecules having sequences at least 90%, 95%, 96%, 97%, 98% or 99% identical to the nucleic acid sequence shown in FIG. 1 (SEQ ID NO:1) or to the nucleic acid sequence of the deposited cDNA which do, in fact, encode a polypeptide having CKα-4 protein activity. By "a polypeptide having CKα-4 activity" is intended polypeptides exhibiting activity similar, but not necessarily identical, to an activity of the CKα-4 protein of the invention (either the full-length protein or, preferably, the mature protein), as measured in a particular biological assay. For example, the CKα-4 protein of the present invention modulates colony formation of bone marrow progenitor cells, as does Human Chemokine HCC-1. An in vitro colony forming assay for measuring the extent of inhibition of myeloid progenitor cells is described in Youn et al., The Journal of Immunology 155:2661–2667 (1995). Briefly, the assay involves collecting human or mouse bone marrow cells and plating the same on agar, adding one or more growth factors and either (1) transfected host cell-supernatant containing CKα-4 protein (or a candidate polypeptide) or (2) nontransfected host cell-supernatant control, and measuring the effect on colony formation by murine and human CFU-granulocyte-macrophages (CFU-GM), by human burst-forming unit-erythroid (BFU-E), or by human CFU granulocyte-erythroid-macrophage-megakaryocyte (CFU-GEMM).

CKα-4 protein modulates immune system cell proliferation and differentiation in a dose-dependent manner in the above-described assay. Thus, "a polypeptide having CKα-4 protein activity" includes polypeptides that also exhibit any of the same immune system cell modulating activities in the above-described assay in a dose-dependent manner. Although the degree of dose-dependent activity need not be identical to that of the CKα-4 protein, preferably, "a polypeptide having CKα-4 protein activity" will exhibit substantially similar dose-dependence in a given activity as compared to the CKα-4 protein (i.e., the candidate polypeptide will exhibit greater activity or not more than about 25-fold less and, preferably, not more than about tenfold less activity relative to the reference CKα-4 protein).

Like other CXC chemokines, CKα-4 exhibits activity on leukocytes including for example monocytes, lymphocytes and neutrophils. For this reason CKCα-4 is active in directing the proliferation, differentiation and migration of these cell types. Such activity is useful for immune enhancement or suppression, myeloprotection, stem cell mobilization, acute and chronic inflammatory control and treatment of leukemia. Assays for measuring such activity are known in the art. For example, see Peters et al., Immun. Today, 17:273 (1996); Young et al., J. Exp. Med., 182:1111 (1995); Caux et al., Nature, 390:258 (1992); and Santiago-Schwarz et al., Adv. Exp. Med. Biol., 378:7 (1995).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIG. 1 (SEQ ID NO:1) will encode a polypeptide "having CKα-4 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having CKα-4 protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," Science 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., supra, and the references cited therein.

Vectors and Host Cells

The present invention also relates to vectors which include the isolated DNA molecules of the present invention, host cells which are genetically engineered with the recombinant vectors, and the production of CKα-4 polypeptides or fragments thereof by recombinant techniques.

Recombinant constructs may be introduced into host cells using well known techniques such as infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate trans-acting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter, such as the phage lambda PL promoter, the *E. coli* lac, trp, phoA and tac promoters, the SV40 early and late promoters, the M promoter, the tetracycline regulated promoter, the actin promoter, and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, Streptomyces and Salmonella typhimurium cells; fungal cells, such as yeast cells; insect cells such as Drosophila S2 and Spodoptera Sf9 cells; animal cells such as CHO, COS, 293 and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNA18A, pNH46A, available from Stratagene; and ptrc99a, pKK223–3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Among known bacterial promoters suitable for use in the present invention include the *E. coli* lacI and lacZ promoters, the T3 and T7 promoters, the gpt promoter, the lambda PR and PL promoters, the phoA promoter and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986).

Transcription of the DNA encoding the polypeptides of the present invention by higher eukaryotes may be increased by inserting an enhancer sequence into the vector. Enhancers are cis-acting elements of DNA, usually about from 10 to 300 bp in length that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, immunoglobulin enhancer and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to stabilize and purify proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example, when the fusion protein is to be used as antigen for immunizations. In drug discovery, for example, human proteins, such as, hIL-5 have been fused with Fc portions for the purpose of high-throughput screening assays to identify antagonists of hIL-5. See, D. Bennett et al., Journal of Molecular Recognition, Vol. 8:52–58 (1995) and K. Johanson et al., The Journal of Biological Chemistry, Vol. 270, No. 16:9459–9471 (1995).

Peptides and polypeptides of the present invention can be produced by chemical synthetic procedures known to those of ordinary skill in the art. For example, polypeptides up to about 80–90 amino acid residues in length may be produced on a commercially available peptide synthesizer model 433A (Applied Biosystems, Inc., Foster City, Calif.). Thus, as will be readily appreciated, the full-length mature CKα-4 polypeptide can be produced synthetically.

The CKα-4 protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinty chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

CKα-4 Polypeptides and Fragments

The invention further provides an isolated CKα-4 polypeptide having the amino acid sequence encoded by the deposited cDNA, or the amino acid sequence in FIG. 1 (SEQ ID NO:2), or a peptide or polypeptide comprising a portion of the above polypeptides. The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

N-Terminal and C-Terminal Deletion Mutants

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron et al., *J. Biol. Chem*., 268:2984–2988 (1993) reported modified KGF proteins that had heparin binding activity even if 3, 8, or 27 amino-terminal amino acid residues were missing. In the present case, since the protein of the invention is a member of the alpha polypeptide family, deletions of N-terminal amino acids up to the cysteine at position 30 of SEQ ID NO:2 may retain some biological activity such as receptor binding or modulation of target cell activities. Polypeptides having further N-terminal deletions including the cysteine at position 30 residue in SEQ ID NO:2 would not be expected to retain such biological activities because it is known that this residue in a chemokine-related polypeptide is required for forming a disulfide bridge to provide structural stability which is needed for receptor binding and signal transduction.

However, even if deletion of one or more amino acids from the N-terminus of a protein results in modification or loss of one or more biological functions of the protein, other biological activities may still be retained. Thus, the ability of the shortened protein to induce and/or bind to antibodies which recognize the complete or mature form of the protein generally will be retained when less than the majority of the residues of the complete or mature protein are removed from the N-terminus. Whether a particular polypeptide lacking N-terminal residues of a complete protein retains such immunologic activities can readily be determined by routine methods described herein and otherwise known in the art.

Accordingly, the present invention further provides polypeptides having one or more residues deleted from the amino terminus of the amino acid sequence of the CKα-4 polypeptide shown in SEQ ID NO:2, up to the cysteine residue at position number 30, and polynucleotides encoding such polypeptides. In particular, the present invention provides polypeptides comprising the amino acid sequence of residues n-94 of SEQ ID NO:2, where n is an integer in the range of 19 to 30, where 30 is the position of the first residue from the N-terminus of the complete CKα-4 polypeptide (shown in SEQ ID NO:2) believed to be required for receptor binding activity of the CKα-4 protein and induction of signal transduction.

More in particular, the invention provides polynucleotides encoding polypeptides having the amino acid sequence of residues 19–94, 20–94, 21–94, 22–94, 23–94, 24–94, 25–94, 26–94, 27–94, 28–94, 29–94 and 30–94 of SEQ ID NO:2. Polynucleotides encoding these polypeptides also are provided.

Similarly, many examples of biologically functional C-terminal deletion muteins are known. For instance, Interferon gamma shows up to ten times higher activities by deleting 8–10 amino acid residues from the carboxy terminus of the protein (Dobeli et al., *J. Biotechnology* 7:199–216 (1988). In the present case, since the protein of the invention is a member of the chemokine polypeptide family, deletions of C-terminal amino acids up to the cysteine residue at position 74 of SEQ ID NO:2 may retain some biological activity such as receptor binding or modulation of target cell activities. Polypeptides having further C-terminal deletions including the cysteine residue at position 74 of SEQ ID NO:2 would not be expected to retain such biological activities because it is known that this residue in a chemokine-related polypeptide is required for forming a disulfide bridge to provide structural stability which is needed for receptor binding and signal transduction.

However, even if deletion of one or more amino acids from the C-terminus of a protein results in modification of loss of one or more biological functions of the protein, other biological activities may still be retained. Thus, the ability of the shortened protein to induce and/or bind to antibodies which recognize the complete or mature form of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art.

Accordingly, the present invention further provides polypeptides having one or more residues from the carboxy terminus of the amino acid sequence of the CKα-4 shown in SEQ ID NO:2, up to the cysteine residue at position 74 of SEQ ID NO:2, and polynucleotides encoding such polypeptides. In particular, the present invention provides polypeptides having the amino acid sequence of residues 19-m of the amino acid sequence in SEQ ID NO:2, where m is any integer in the range of 74–94, and residue 74 is the position of the first residue from the C- terminus of the complete CKα-4 polypeptide (shown in SEQ ID NO:2) believed to be required for receptor binding and signal transduction of the CKα-4 protein.

More in particular, the invention provides polynucleotides encoding polypeptides having the amino acid sequence of residues 19–74, 19–75, 19–76, 19–77, 19–78, 19–79, 19–80, 19–81, 19–82, 19–83, 19–84, 19–85, 19–86, 19–87, 19–88, 89, 19–90, 19–91, 19–92, 19–93 and 19–94 of SEQ ID NO:2. Polynucleotides encoding these polypeptides also are provided.

The invention also provides polypeptides having one or more amino acids deleted from both the amino and the carboxyl termini, which may be described generally as having residues n-m of SEQ ID NO:2, where n and m are integers as described above. Also included are a nucleotide sequence encoding a polypeptide consisting of a portion of the complete CKα-4 amino acid sequence encoded by the cDNA clone contained in ATCC Deposit No. 97692, where this portion excludes from 18 to about 29 amino acids from the amino terminus of the complete amino acid sequence encoded by the cDNA clone contained in ATCC Deposit No. 97692, or from 1 to about 20 amino acids from the carboxy terminus, or any combination of the above amino terminal and carboxy terminal deletions, of the complete amino acid sequence encoded by the cDNA clone contained in ATCC Deposit No. 97692. Polynucleotides encoding all of the above deletion mutant polypeptide forms also are provided.

In addition to mature and N-terminal deletion forms of the protein discussed above, it will be recognized by one of ordinary skill in the art that some amino acid sequences of the CKα-4 polypeptide can be varied without significant effect of the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of the CKα-4 polypeptide which show substantial CKα-4 polypeptide activity or which include regions of CKα-4 protein such as the protein portions discussed below. Such mutants include deletions, insertions, inversions, repeats, and type substitutions (for example, substituting one hydrophilic residue for another, but not strongly hydrophilic or strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Be; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

As indicated in detail above, further guidance concerning which amino acid changes are likely to be phenotypically silent (i.e., are not likely to have a significant deleterious effect on a function) can be found in Bowie, J. U., et al., "Deciphering the Message in Protein Sequences: Tolerance to Amino Acid Substitutions," Science 247:1306–1310 (1990).

The polypeptides of the present invention are preferably provided in an isolated form, and preferably are substantially purified. A recombinantly produced version of the CKα-4 polypeptide can be substantially purified by the one-step method described in Smith and Johnson, Gene 67:3140 (1988).

The polypeptides of the present invention include the polypeptide encoded by the deposited cDNA including the leader, the mature polypeptide encoded by the deposited cDNA minus the leader (i.e., the mature protein), the polypeptide of FIG. 1 (SEQ ID NO:2) including the leader, the polypeptide of FIG. 1 (SEQ ID NO:2) minus the leader, as well as polypeptides which have at least 90% similarity, more preferably at least 95% similarity, and still more preferably at least 96%, 97%, 98% or 99% similarity to those described above. Further polypeptides of the present invention include polypeptides at least 80% identical, more preferably at least 90% or 95% identical, still more preferably at least 96%, 97%, 98% or 99% identical to the polypeptide encoded by the deposited cDNA, to the polypeptide of FIG. 1 (SEQ ID NO:2), and also include portions of such polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482489, 1981) to find the best segment of similarity between two sequences.

By a polypeptide having an amino acid sequence at least, for example, 95% "identical" to a reference amino acid sequence of a CKα-4 polypeptide is intended that the amino acid sequence of the polypeptide is identical to the reference sequence except that the polypeptide sequence may include up to five amino acid alterations per each 100 amino acids of the reference amino acid of the CKα-4 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIG. 1 (SEQ ID NO:2) or to the amino acid sequence encoded by deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting CKα-4 protein expression as described below or as agonists and antagonists capable of enhancing or inhibiting CKα-4 protein function. Further, such polypeptides can be used in the yeast two-hybrid system to "capture" CKα-4 protein binding proteins which are also candidate agonist and antagonist according to the present invention. The yeast two hybrid system is described in Fields and Song, Nature 340:245–246 (1989).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen et al., Proc. Natl. Acad. Sci. USA 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) "Antibodies that react with predetermined sites on proteins", Science, 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, peptides, especially those containing proline residues, usually are effective. Sutcliffe et al., supra, at 661. For instance, 18 of 20 peptides designed according to these guidelines, containing 8–39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson et al., Cell 37:767–778 (1984) at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

Non-limiting examples of antigenic polypeptides or peptides that can be used to generate CKa- 4specific antibodies include: a polypeptide comprising amino acid residues from about Pro 23 to about Cys 32 in FIG. 1 (SEQ ID NO:2); a polypeptide comprising amino acid residues from about Pro 35 to about Ser 49 in FIG. 1 (SEQ ID NO:2); a polypeptide comprising amino acid residues from about Tyr 52 to about Val 62 in FIG. 1 (SEQ ID NO:2); and a polypeptide comprising amino acid residues from about Leu 66 to about Phe 94 in FIG. 1 (SEQ ID NO:2) As indicated above, the inventor has determined that the above polypeptide fragments are antigenic regions of the CKα-4 protein.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks. Houghten, R. A. (1985) General method for the rapid solid-phase synthesis of large numbers of peptides: specificity of antigen-antibody interaction at the level of individual amino acids. Proc. Natl. Acad. Sci. USA 82:5131–5135. This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously. Houghten et al., supra, at 5134.

The major predicted antigenic peptide regions are defined by FIG. 2 (SEQ ID NO:2) as follows:

| Amino Acids | Antigenicity |
|---|---|
| 23–32 | Stronger |
| 35–49 | Weaker |
| 52–62 | Stronger |
| 66–94 | Stronger |

Epitope-bearing peptides and polypeptides of the invention are used to induce antibodies according to methods well known in the art. See, for instance, Sutcliffe et al., supra; Wilson et al., supra; Chow, M. et al., Proc. Natl. Acad. Sci. USA 82:910–914; and Bittle, F. J. et al., J. Gen. Virol. 66:2347–2354 (1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to a carrier using a linker such as m-maleimidobenzoyl-N-hydroxysuccimide ester (MBS), while other peptides may be coupled to a carrier using a more general linking agent such as glutaraldehyde. Animals such as rabbits, rats and mice are immunized with either free or carrier-coupled peptides, for instance, by intraperitoneal and/or intradermal injection of emulsions containing about 100 g peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear C1–C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

The entire disclosure of each document cited in this section on "Polypeptides and Peptides" is hereby incorporated herein by reference.

As one of skill in the art will appreciate, CKα-4 polypeptides of the present invention and the epitope-bearing fragments thereof described above can be combined with parts of the constant domain of immunoglobulin (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker et al., Nature 331:84–86 (1988)). Fusion proteins that have a disulfide-linked dimeric structure due to the IgG part can also be more efficient in binding and neutralizing other molecules than the monomeric CKα-4 protein or protein fragment alone (Fountoulakis et al., J. Biochem. 270:3958–3964 (1995)).

Immune System-Related Disorder Diagnosis

The present inventors have discovered that CKα-4 is expressed in gamma-interferon induced epithelial cells and T-cell lymphoma tissue. For a number of immune system-related disorders, substantially altered (increased or decreased) levels of CKα-4 gene expression can be detected in immune system tissue wounded tissue, cancerous tissue or other cells or bodily fluids (e.g., sera, plasma, urine, synovial fluid or spinal fluid) taken from an individual having such a disorder, relative to a "standard" CKα-4 gene expression level, that is, the CKα-4 expression level in immune system tissues or bodily fluids from an individual not having the immune system disorder. Thus, the invention provides a diagnostic method useful during diagnosis of an immune system disorder, which involves measuring the expression level of the gene encoding the CKα-4 protein in immune system tissue or other cells or body fluid from an individual and comparing the measured gene expression level with a standard CKα-4 gene expression level, whereby an increase or decrease in the gene expression level compared to the standard is indicative of an immune system disorder.

By individual is intended mammalian individuals, preferably humans. By "measuring the expression level of the gene encoding the CKα-4 protein" is intended qualitatively or quantitatively measuring or estimating the level of the CKα-4 protein or the level of the mRNA encoding the CKα-4 protein in a first biological sample either directly (e.g., by determining or estimating absolute protein level or mRNA level) or relatively (e.g., by comparing to the CKα-4 protein level or mRNA level in a second biological sample). Preferably, the CKα-4 protein level or mRNA level in the first biological sample is measured or estimated and compared to a standard CKα-4 protein level or mRNA level, the standard being taken from a second biological sample obtained from an individual not having the disorder or being determined by averaging levels from a population of individuals not having a disorder of the immune system. As will be appreciated in the art, once a standard CKα-4 protein level or mRNA level is known, it can be used repeatedly as a standard for comparison.

By "biological sample" is intended any biological sample obtained from an individual, body fluid, cell line, tissue culture, or other source which contains CKα-4 protein or mRNA. As indicated, biological samples include body fluids (such as sera, plasma, urine, synovial fluid and spinal fluid) which contain secreted mature CKα-4 protein, immune system tissue, and other tissue sources found to express CKα-4 or a CKα-4 receptor. Methods for obtaining tissue biopsies and body fluids from mammals are well known in the art. Where the biological sample is to include mRNA, a tissue biopsy is the preferred source.

The present invention is useful for diagnosis or treatment of various immune system-related disorders in mammals, preferably humans. Such disorders include tumors, cancers, interstitial lung disease (such as Langerhans cell granulomatosis) and any disregulation of immune cell function including, but not limited to, autoimmunity, arthritis, leukemias, lymphomas, immunosuppression, immunity, humoral immunity, inflammatory bowel disease, myelosuppression, and the like.

Total cellular RNA can be isolated from a biological sample using any suitable technique such as the single-step guanidinium-thiocyanate-phenol-chloroform method described in Chomczynski and Sacchi, Anal. Biochem. 162:156–159 (1987). Levels of mRNA encoding the CKα-4 protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al., Cell 63:303–312 (1990). Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. CKα-4 protein cDNA labeled according to any appropriate method (such as the 32P-multiprimed DNA labeling system (Amersham)) is used as probe. After hybridization overnight, the filter is washed and exposed to x-ray film. cDNA for use as probe according to the present invention is described in the sections above and will preferably be at least 15 bp in length.

S1 mapping can be performed as described in Fujita et al., Cell 49:357–367 (1987). To prepare probe DNA for use in S1 mapping, the sense strand of above-described cDNA is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding the CKα-4 protein). Northern blot analysis can be performed as described above.

Preferably, levels of mRNA encoding the CKα-4 protein are assayed using the RT-PCR method described in Makino et al., Technique 2:295–301 (1990). By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the CKα-4 protein)) is quantified using an imaging analyzer. RT and PCR reaction ingredients and conditions, reagent and gel concentrations, and labeling methods are well known in the art. Variations on the RT-PCR method will be apparent to the skilled artisan.

Any set of oligonucleotide primers which will amplify reverse transcribed target mRNA can be used and can be designed as described in the sections above.

Assaying CKα-4 protein levels in a biological sample can occur using any art-known method. Preferred for assaying CKα-4 protein levels in a biological sample are antibody-based techniques. For example, CKα-4 protein expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of CKα-4 protein for Western-blot or dot/slot assay (Jalkanen, M., et al., J. Cell. Biol. 101:976–985 (1985); Jalkanen, M., et al., J. Cell. Biol. 105:3087–3096 (1987)). In this technique, which is based on the use of cationic solid phases, quantitation of CKα-4 protein can be accomplished using isolated CKα-4 protein as a standard. This technique can also be applied to body fluids. With these samples, a molar concentration of CKα-4 protein will aid to set standard values of CKα-4 protein content for different body fluids, like serum, plasma, urine, spinal fluid, etc. The normal appearance of CKα-4 protein amounts can then be set using values from healthy individuals, which can be compared to those obtained from a test subject.

Other antibody-based methods useful for detecting CKα-4 protein gene expression include immunoassays, such as the enzyme linked immunosorbent assay (ELISA) and the radioimmunoassay (RIA). For example, a CKα-4 protein-specific monoclonal antibody can be used both as an immunoabsorbent and as an enzyme-labeled probe to detect and quantify the CKα-4 protein. The amount of CKα-4 protein present in the sample can be calculated by reference to the amount present in a standard preparation using a linear regression computer algorithm. Such an ELISA for detecting a tumor antigen is described in Iacobelli et al., Breast Cancer Research and Treatment 11:19–30 (1988). In another ELISA assay, two distinct specific monoclonal antibodies can be used to detect CKα-4 protein in a body fluid. In this assay, one of the antibodies is used as the immunoabsorbent and the other as the enzyme-labeled probe.

The above techniques may be conducted essentially as a "one-step" or "two-step" assay. The "one-step" assay involves contacting CKα-4 protein with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labelled antibody/substrate reaction. Besides enzymes, other suitable labels include radioisotopes, such as iodine (125I, 121I), carbon (14C), sulfur (35S), tritium (3H), indium (112In), and technetium (99mTc), and fluorescent labels, such as fluorescein and rhodamine, and biotin.

In addition to assaying CKα-4 protein levels in a biological sample obtained from an individual, CKα-4 protein can also be detected in vivo by imaging. Antibody labels or markers for in vivo imaging of CKα-4 protein include those detectable by X-radiography, NMR or ESR. For X-radiography, suitable labels include radioisotopes such as barium or caesium, which ernit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A CKα-4 protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally; subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain CKα-4 protein. In vivo tumor imaging is described in S. W. Burchiel et al., "Immunopharmacokinetics of Radiolabelled Antibodies and Their Fragments" (Chapter 13 in Tumor Imaging: The Radiochemical Detection of Cancer, S. W. Burchiel and B. A. Rhodes, eds., Masson Publishing Inc. (1982)).

CKa- 4-protein specific antibodies for use in the present invention can be raised against the intact CKα-4 protein or an antigenic polypeptide fragment thereof, which may be presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')2 fragments) which are capable of specifically binding to CKα-4 protein. Fab and F(ab')2 fragments lack the Fc fragment of intact antibody, clear more rapidly from the circulation, and may have less non-specific tissue binding of an intact antibody (Wahl et al., J. Nucl. Med. 24:316–325 (1983)). Thus, these fragments are preferred.

The antibodies of the present invention may be prepared by any of a variety of methods. For example, cells expressing the CKα-4 protein or an antigenic fragment thereof can be administered to an animal in order to induce the production of sera containing polyclonal antibodies. In a preferred method, a preparation of CKα-4 protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or CKα-4 protein binding fragments thereof). Such monoclonal antibodies can be prepared using hybridoma technology (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., (1981) pp. 563–681 ). In general, such procedures involve immunizing an animal (preferably a mouse) with a CKα-4 protein antigen or, more preferably, with a CKα-4 protein-expressing cell. Suitable cells can be recognized by their capacity to bind anti-CKα-4 protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 μg/l of nonessential amino acids, about 1,000 U/ml of penicillin, and about 100 μg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP2O), available from the American Type Culture Collection, Rockville, Md. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the CKα-4 protein antigen.

Alternatively, additional antibodies capable of binding to the CKα-4 protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, CKα-4-protein specific antibodies are used to immunize an animal, preferably a mouse. The splenocytes of such an animal are then used to produce hybridoma cells, and the hybridoma cells are screened to identify clones which produce an antibody whose ability to bind to the CKα-4 protein-specific antibody can be blocked by the CKα-4 protein antigen. Such antibodies comprise anti-idiotypic antibodies to the CKα-4 protein-specific antibody and can be used to immunize an animal to induce formation of further CKα-4 protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, CKα-4 protein-binding fragments can be produced through the application of recombinant DNA technology or through synthetic chemistry.

Where in vivo imaging is used to detect enhanced levels of CKα-4 protein for diagnosis in humans, it may be preferable to use "humanized" chimeric monoclonal antibodies. Such antibodies- can be produced using genetic constructs derived from hybridoma cells producing the monoclonal antibodies described above. Methods for producing chimeric antibodies are known in the art. See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).

Further suitable labels for the CKα-4 protein-specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include 3H, 111In, 125I, 131I, 32P, 35S, 14C, 51Cr, 57To, 58Co, 59Fe, 75Se, 152Eu, 90Y, 67Cu, 217Ci, 211At, 212Pb, 47Sc, 109Pd, etc. 111In is a preferred isotope where in vivo imaging is used since it avoids the problem of dehalogenation of the 125 I or 131I-labeled monoclonal antibody by the liver. In addition, this radionucleotide has a more favorable gamma emission energy for imaging (Perkins et al., Eur. J. Nucl. Med. 10:296–301 (1985); Carasquillo et al., J. Nucl. Med. 28:281–287 (1987)). For example, 111In coupled to monoclonal antibodies with 1-(P-isothiocyanatobenzyl)-DPTA has shown little uptake in non-tumorous tissues, particularly the liver, and therefore enhances specificity of tumor localization (Esteban et al., J. Nucl. Med. 28:861–870 (1987)).

Examples of suitable non-radioactive isotopic labels include 157Gd, 55Mn, 162Dy, 52Tr, and 56Fe.

Examples of suitable fluorescent labels include an 152Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to antibodies are provided by Kennedy et al., Clin. Chim. Acta 70:1–31 (1976), and Schurs et al., Clin. Chim. Acta 81:140 (1977). Coupling techniques mentioned in the latter are the glutaraldehyde method, the periodate method, the dimaleimide method, the m-maleimidobenzyl-N-hydroxy-succinimide ester method, all of which methods are incorporated by reference herein.

Treatment of Immune System-Related Disorders

As noted above, CKα-4 lacks the ELR motif immediately preceding the first cysteine residue. Of the known alpha family chemokines, ten of them contain an ELR motif (IL-8, ENA-78, GCP2, GRO-a, GRO-β, GRO-g, PBP, CTAP-III, β-TG, NAP-2) and three lack the ELR motif (IP-10, PF4 and MIG). It has been clearly shown that this ELR motif is required for the neutrophil and endothelial cell chemotactic activity as well as the angiogenic activity of IL-8 (Strieter et al., J. Biol. Chem., 270:27348–27357 (1995)). In addition, it has been shown that the ELR-CXC chemokines have in vitro and in vivo angiogeruc activity, whereas the CXC chemokines lacking the ELR motif are actually angiostatic (Strieter et al., supra; Angiolillo et al., J. Exp. Med., 182:155–162 (1995); and Koch et al., Science, 258:1798–1801 (1992)). In terms of a possible role of such factors in tumor angiogenesis, Smith et al., J. Exp. Med., 179:1409–1415 (1994), has reported increased IL-8 levels in bronchogeneic carcinoma tumor tissues which appear to be produced from the tumor cells. Therefore, CKα-4 is particularly active in modulating activities such as those described above in relation to the description of a "polypeptide having CKα-4 activity." Given the activities modulated by CKα-4, it is readily apparent that a substantially altered (increased or decreased) level of expression of CKα-4 in an individual compared to the standard or "normal" level produces pathological conditions such as those described above in relation to diagnosis of immune system-related disorders. It will also be appreciated by one of ordinary skill that, since the CKα-4 protein of the invention is translated with a leader peptide suitable for secretion of the mature protein from the cells which express CKα-4, when CKα-4 protein (particularly the mature form) is added from an exogenous source to cells, tissues or the body of an individual, the protein will exert its modulating activities on any of its target cells of that individual. Therefore, it will be appreciated that conditions caused by a decrease in the standard or normal level of CKα-4 activity in an individual, particularly disorders of the immune system, can be treated by administration of CKα-4 protein. Thus, the invention also provides a method of treatment of an individual in need of an increased level of CKα-4 activity comprising administering to such an individual a pharmaceutical composition comprising an amount of an isolated CKα-4 polypeptide of the invention, particularly a mature form of the CKα-4 protein of the invention, effective to increase the CKα-4 activity level in such an individual.

Since CKα-4 lacks an ELR motif, it also should be an angiostatic factor rather than an angiogenic factor. In addition, since CKα-4 inhibits endothelial cell function, it will have a wide range of anti-inflammatory activities.

CKα-4 may be employed as an anti-neovascularizing agent to treat solid tumors by stimulating the invasion and activation of host defense cells, e.g., cytotoxic T cells and macrophages and by inhibiting the angiogenesis of tumors. Those of skill in the art will recognize other non-cancer indications where blood vessel proliferation is not wanted. They may also be employed to enhance host defenses against resistant chronic and acute infections, for example, myobacterial infections via the attraction and activation of microbicidal leukocytes.

CKα-4 may also be employed to inhibit T-cell proliferation by the inhibition of IL-2 biosynthesis for the treatment of T-cell mediated auto-immune diseases and lymphocytic leukemias.

CKα-4 may also be employed to stimulate wound healing, both via the recruitment of debris clearing and connective tissue promoting inflammatory cells and also via its control of excessive TGFO-mediated fibrosis. In this same manner, CKα-4 may also be employed to treat other fibrotic disorders, including liver cirrhosis, osteoarthritis and pulmonary fibrosis.

CKα-4 also increases the presence of eosinophils which have the distinctive function of killing the larvae of parasites that invade tissues, as in schistosomiasis, trichinosis and ascariasis.

It may also be employed to regulate hematopoiesis, by regulating the activation and differentiation of various hematopoietic progenitor cells, for example, to release mature leukocytes from the bone marrow following chemotherapy, i.e., in stem cell mobilization.

CKα-4 may also be employed to treat sepsis.

Also, by making a specific mutation to include an ELR motif, CKα-4-ELR will have angiogenic activities which are useful for treating all of the disease states where angiogenesis would be beneficial, i.e., to promote wound healing, re-vascularization of damaged limbs from injury or disease, and others known to those of skill in the art.

The CKα-4 polypeptide composition will be formulated and dosed in a fashion consistent with good medical practice, taking into account the clinical condition of the individual patient (especially the side effects of treatment with CKα-4 polypeptide alone), the site of delivery of the CKα-4 polypeptide composition, the method of administration, the scheduling of administration, and other factors known to practitioners. The "effective amount" of CKα-4 polypeptide for purposes herein is thus determined by such considerations.

As a general proposition, the total pharmaceutically effective amount of CKα-4 polypeptide administered parenterally per dose will be in the range of about 1 μg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the CKα-4 polypeptide is typically administered at a dose rate of about 1 μg/kg/hour to about 50 μg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the CKα-4 of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The CKα-4 polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547–556. (1983)), poly (2- hydroxyethyl methacrylate) (R. Langer et al., J. Biomed. Mater. Res. 15:167–277 (1981), and R. Langer, Chem. Tech. 12:98–105 (1982)), ethylene vinyl acetate (R. Langer et al., Id.) or poly-D- (−)-3-hydroxybutyric acid (EP 133,988). Sustained-release CKα-4 polypeptide compositions also include liposomally entrapped CKα-4 polypeptide. Liposomes containing CKα-4 polypeptide are prepared by methods known per se: DE 3,218,121; Epstein et al., Proc. Natl. Acad. Sci. (USA) 82:3688–3692 (1985); Hwang et al., Proc. Natl. Acad. Sci. (USA) 77:4030–4034 (1980); EP 52,322; EP 36,676; EP 88,046; EP 143,949; EP 142,641; Japanese Pat. Appl. 83–118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal CKα-4 polypeptide therapy.

For parenteral administration, in one embodiment, the CKα-4 polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the CKα-4 polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyargine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium;

and/or nonionic surfactants such as polysorbates, poloxamers, or PEG.

The CKα-4 polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of CKα-4 polypeptide salts.

CKα-4 polypeptide to be used for therapeutic administration must be sterile. Sterility is readily accomplished by filtration through sterile filtration membranes (e.g., 0.2 micron membranes). Therapeutic CKα-4 polypeptide compositions generally are placed into a container having a sterile access port, for example, an intravenous solution bag or vial having a stopper pierceable by a hypodermic injection needle.

CKα-4 polypeptide ordinarily will be stored in unit or multi-dose containers, for example, sealed ampoules or vials, as an aqueous solution or as a lyophilized. formulation for reconstitution. As an example of a lyophilized formulation, 10-ml vials are filled with 5 ml of sterile-filtered 1% (w/v) aqueous CKα-4 polypeptide solution, and the resulting mixture is lyophilized. The infusion solution is prepared by reconstituting the lyophilized CKα-4 polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Agonists and Antagonists—Assays and Molecules

The invention also provides a method of screening compounds to identify those which enhance or block the action of CKα-4 on cells, such as its interaction with CKα-4-binding molecules such as receptor molecules. An agonist is a compound which increases the natural biological functions of CKα-4 or which functions in a manner similar to CKα-4, while antagonists decrease or eliminate such functions.

For example, a cellular compartment, such as a membrane or a preparation thereof, such as a membrane-preparation, may be prepared from a cell that expresses a molecule that binds CKα-4, such as a molecule of a signaling or regulatory pathway modulated by CKα-4. The preparation is incubated with labeled CKα-4 in the absence or the presence of a candidate molecule which may be a CKα-4 agonist or antagonist. The ability of the candidate molecule to bind the binding molecule is reflected in decreased binding of the labeled ligand. Molecules which bind gratuitously, i.e., without inducing the effects of CKα-4 on binding the CKα-4 binding molecule, are most likely to be good antagonists. Molecules that bind well and elicit effects that are the same as or closely related to CKα-4 are agonists.

CKα-4-like effects of potential agonists and antagonists may by measured, for instance, by determining activity of a second messenger system following interaction of the candidate molecule with a cell or appropriate cell preparation, and comparing the effect with that of CKa- 4 or molecules that elicit the same effects as CKα-4. Second messenger systems that may be useful in this regard include but are not limited to AMP guanylate cyclase, ion channel or phosphoinositide hydrolysis second messenger systems.

Another example of an assay for CKα-4 antagonists is a competitive assay that combines CKα-4 and a potential antagonist with membrane-bound CKα-4 receptor molecules or recombinant CKα-4 receptor molecules under appropriate conditions for a competitive inhibition assay. CKα-4 can be labeled, such as by radioactivity, such that the number of CKα-4 molecules bound to a receptor molecule can be determined accurately to assess the effectiveness of the potential antagonist.

Potential antagonists include small organic molecules, peptides, polypeptides and antibodies, that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing CKα-4-induced activities, thereby preventing the action of CKα-4 by excluding CKα-4 from binding.

Other potential antagonists include antisense molecules. Antisense technology can be used to control gene expression through antisense DNA or RNA or through triple-helix formation. Antisense techniques are discussed, for example, in Okano, J. Neurochem. 56: 560 (1991); "Oligodeoxynucleotides as Antisense Inhibitors of Gene Expression, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA ofigonucleotide is designed to be complementary to a region of the gene involved in transcription thereby preventing transcription and the production of CKα-4. The antisense RNA oligonucleotide hybridizes to the mRNA in vivo and blocks translation of the mRNA molecule into CKα-4 polypeptide. The oligonucleotides described above can also be delivered to cells such that the antisense RNA or DNA may be expressed in vivo to inhibit production of CKα-4.

The antagonists may be employed in a composition with a pharmaceutically acceptable carrier, e.g., as described above.

The antagonists may be employed for instance to inhibit the chemotaxis and activation of macrophages and their precursors, and of neutrophils, basophils, B lymphocytes and some T-cell subsets, e.g., activated and CD8 cytotoxic T cells and natural killer cells, in certain auto-immune and chronic inflammatory and infective diseases. Examples of auto-immune diseases include multiple sclerosis, and insulin-dependent diabetes.

The antagonists may also be employed to treat infectious diseases including silicosis, sarcoidosis, idiopathic pulmonary fibrosis by preventing the recruitment and activation of mononuclear phagocytes. They may also be employed to treat idiopathic hyper-eosinophilic syndrome by preventing eosinophil production and migration. Endotoxic shock may also be treated by the antagonists by preventing the migration of macrophages and their production of the human chemokine polypeptides of the present invention.

The antagonists may also be employed for treating atherosclerosis, by preventing monocyte infiltration in the artery wall.

The antagonists may also be employed to treat histamine-mediated allergic reactions and immunological disorders including late phase allergic reactions, chronic urticaria, and atopic dermatitis by inhibiting chemokine-induced mast cell and basophil degranulation and release of histamine. IgE-mediated allergic reactions such as allergic asthma, rhinitis, and eczema may also be treated.

The antagonists may also be employed to treat chronic and acute inflammation by preventing the attraction of monocytes to a wound area. They may also be employed to regulate normal pulmonary macrophage populations, since chronic and acute inflammatory pulmonary diseases are associated with sequestration of mononuclear phagocytes in the lung.

Antagonists may also be employed to treat rheumatoid arthritis by preventing the attraction of monocytes into synovial fluid in the joints of patients. Monocyte influx and activation plays a significant role in the pathogenesis of both degenerative and inflammatory arthropathies.

The antagonists may be employed to interfere with the deleterious cascades attributed primarily to IL-1 and TNF, which prevents the biosynthesis of other inflammatory cytokines. In this way, the antagonists may be employed to prevent inflammation. The antagonists may also be employed to inhibit prostaglandin-independent fever induced by chemokines.

The antagonists may also be employed to treat cases of bone marrow failure, for example, aplastic anemia and myelodysplastic syndrome.

The antagonists may also be employed to treat asthma and allergy by preventing eosinophil accumulation in the lung. The antagonists may also be employed to treat subepithelial basement membrane fibrosis which is a prominent feature of the asthmatic lung.

Antibodies against CKα-4 may be employed to bind to and inhibit CKα-4 activity to treat ARDS, by preventing infiltration of neutrophils into the lung after injury.

The antagonists may be employed in a composition with a pharmaceutically acceptable carrier, e.g., as hereinafter described.

Chromosome Assays

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a CKα-4 protein gene. This can be accomplished using a variety of well known techniques and libraries, which generally are available commercially. The genomic DNA then is used for in situ chromosome mapping using well known techniques for this purpose. Typically, in accordance with routine procedures for chromosome mapping, some trial and error may be necessary to identify a genoric probe that gives a good in situ hybridization signal.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified portion.

PCR mapping of somatic cell hybrids is a rapid procedure for assigning a particular DNA to a particular chromosome. Using the present invention with the same oligonucleotide primers, sublocalization can be achieved with panels of portions from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., Human Chromosomes: A Manual Of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance In Man, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. This assumes 1 megabase mapping resolution and one gene per 20 kb.

Having generally described the invention, the same will be more readily understood by reference to the following examples, which are provided by way of illustration and are not intended as limiting.

EXAMPLES

Example 1

Expression and Purification of CKα-4 in *E. coli*

The DNA sequence encoding the CKα-4 protein in the deposited cDNA clone is amplified using PCR oligonucleotide primers specific to the amino terminal sequences of the CKα-4 protein and to vector sequences 3' to the gene. Additional nucleotides containing restriction sites to facilitate cloning are added to the 5' and 3' sequences respectively.

The 5' oligonucleotide primer has the sequence 5' gactcatgacagttgttcaaggctcc 3' (SEQ ID NO:4) containing the underlined BspHI restriction site.

The 3' primer has the sequence 5' gacagatctttaaaaattctttctttcaactt 3' (SEQ ID NO:5) containing the underlined BglII restriction site.

The restriction sites are convenient to restriction enzyme sites in the bacterial expression vector pQE60, which are used for bacterial expression in these examples. (Qiagen, Inc. 9259 Eton Avenue, Chatsworth, Calif., 91311). pQE60 encodes ampicillin antibiotic resistance ("Ampr") and contains a bacterial origin of replication ("ori"), an IPTG inducible promoter, a ribosome binding site ("RBS"), a 6-His tag and restriction enzyme sites.

The amplified CKα-4 DNA is digested with BspHI and BglII. The vector pQE60 is digested with NcoI and BglI and the digested DNAs are then ligated together. Insertion of the CKα-4 protein DNA into the restricted pQE60 vector places the CKα-4 protein coding region downstream of and operably linked to the vector's IPTG-inducible promoter and in-frame with an initiating AUG, introduced by the primer, appropriately positioned for translation of CKα-4 protein.

The ligation mixture is transformed into competent *E. coli* cells using standard procedures. Such procedures are described in Sambrook et al., Molecular Cloning: a Laboratory Manual, 2nd Ed.; Cold Spring Harbor Laboratory Press, Cold Spring Harbor, N.Y. (1989). *E. coli* strain M15/rep4, containing multiple copies of the plasmid pREP4, which expresses lac repressor and confers kanamycin resistance ("Kanr"), is used in carrying out the illustrative example described herein. This strain, which is only one of many that are suitable for expressing CKα-4 protein, is available commercially from Qiagen.

Transformants are identified by their ability to grow on LB plates in the presence of ampicillin and kanamycin. Plasmid DNA is isolated from resistant colonies and the identity of the cloned DNA confirmed by restriction analysis.

Clones containing the desired constructs are grown overnight ("O/N") in liquid culture in LB media supplemented with both ampicillin (100 μg/ml) and kanamycin (25 μg/ml).

The O/N culture is used to inoculate a large culture, at a dilution of approximately 1:20 to 1:250. The cells are grown to an optical density at 600 nm ("OD600") of between 0.4 and 0.6. Isopropyl-β-D-thiogalactopyranoside ("IPTG") is then added to a final concentration of 1 mM to induce transcription from lac repressor sensitive promoters, by inactivating the lacI repressor. Cells subsequently are incubated further for 3 to 4 hours. Cells then are harvested by centrifugation and disrupted, by standard methods. Inclusion bodies are purified from the disrupted cells using routine collection techniques, and protein is solubilized from the inclusion bodies into 8M urea. The 8M urea solution containing the solubilized protein is passed over a PD-10 column in 2×phosphate-buffered saline ("PBS"), thereby removing the urea, exchanging the buffer and refolding the protein. The protein is purified by a further step of chromatography to remove endotoxin. Then, it is sterile filtered. The sterile filtered protein preparation is stored in 50 mM sodium acetate, 100 mM NaCl, pH 6.0 at a concentration of 0.1–5.0 μg/ml.

Example 2

Cloning and Expression of CKα-4 Protein in a Baculovirus Expression System

The cDNA sequence encoding the full length CKα-4 protein in the deposited clone is amplified using PCR oligonucleotide primers corresponding to the 5' and 3' sequences of the gene:

The 5' primer has the sequence 5' gactggatccgccatcatgagtgtgaagggcatgg 3' (SEQ ID NO:6) containing the underlined BamI restriction enzyme site. The 5' end of the amplified fragment encoding CKα-4 provides an efficient signal for initiation of translation in eukaryotic cells, as described by Kozak, M., J. Mol. Biol. 196:947–950 (1987).

The 3' primer has the sequence 5' gactggtacccagatgctcttttccaggac 3' (SEQ ID NO:7) containing the underlined Asp718 restriction site.

The amplified fragment is isolated from a 1% agarose gel using a commercially available kit ("Geneclean," BIO 101 Inc., La Jolla, Calif.). The fragment then is digested with BamHI and Asp718 and again is purified on a 1% agarose gel.

The vector pA2 is used to express the CKα-4 protein in the baculovirus expression system, using standard methods, as described in Summers et al., A Manual of Methods for Baculovirus Vectors and Insect Cell Culture Procedures, Texas Agricultural Experimental Station Bulletin No. 1555 (1987). This expression vector contains the strong polyhedrin promoter of the Autographa californica nuclear polyhedrosis virus (AcMNPV) followed by convenient restriction sites, such as BamHI, XbaI and Asp718. The polyadenylation site of the simian virus 40 ("SV40") is used for efficient polyadenylation. For an easy selection of recombinant virus the beta-galactosidase gene from *E. coli* is inserted in the same orientation as the polyhedrin promoter and is followed by the polyadenylation signal of the polyhedrin gene. The polyhedrin sequences are flanked at both sides by viral sequences for cell-mediated homologous recombination with wild-type viral DNA to generate viable virus that express the cloned polynucleotide.

Many other baculovirus vectors could be used in place of pA2, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., Virology 170: 31–39, among others.

The plasmid is digested with the restriction enzyme BamHI and Asp718 and then is dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment encoding CKα-4 and the dephosphorylated linear plasmid are ligated together with T4 DNA ligase. *E. coli* HB 101 cells are transformed with ligation mix and spread on culture plates. Bacteria are identified that contain the plasmid with the human CKα-4 gene by digesting DNA from individual colonies using BamHI and Asp718 and then analyzing the digestion product by gel electrophoresis or by PCR using the primers identified by SEQ ID NOs:6 and 7. The sequence of the cloned fragment is confirmed by DNA sequencing. This plasmid is designated herein pBacCKa-4.

5 μg of the plasmid pBacCKα-4 is co-transfected with 1.0 μg of a commercially available linearized baculovirus DNA ("BaculoGold™ baculovirus DNA", Pharmingen, San Diego, Calif.), using the lipofection method described by Felgner et al., Proc. Natl. Acad. Sci. USA 84: 7413–7417 (1987). 1 μg of BaculoGold™ virus DNA and 5 μg of the plasmid pBacCKα-4 are mixed in a sterile well of a microtiter plate containing 50 μl of serum-free Grace's medium (Life Technologies Inc., Gaithersburg, Md.). Afterwards 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium suppleniented with 10% fetal calf serum is added. The plate is put back into an incubator and cultivation is continued at 27° C. for four days.

After four days the supernatant is collected and a plaque assay is performed, as described by Summers and Smith, cited above. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10).

After appropriate incubation, blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculovirus is used to infect Sf9 cells seeded in 35 mm dishes. Four days later the supernatants of these culture dishes are harvested and then they are stored at 4° C. A virus containing properly inserted CKα-4 is identified by DNA analysis including restriction mapping and sequencing. This is designated herein as V-CKα-4.

Sf9 cells are grown in Grace's medium supplemented with 10% heat-inactivated FBS. The cells are infected with the recombinant baculovirus V-CKα-4 at a multiplicity of infection ("MOI") of about 2 (about 1 to about 3). Six hours later the medium is removed and is replaced with SF900 II medium minus methionine and cysteine (available from Life Technologies Inc., Gaithersburg). 42 hours later, 5 μCi of 35S-methionine and 5 μCi 35S-cysteine (available from Amersham) are added. The cells are further incubated for 16 hours and then they are harvested by centrifugation and lysed. The labeled proteins from both the lysed cells and the supernatant are visualized by SDS-PAGE and autoradiography.

Example 3

Cloning and Expression in Mammalian Cells

Most of the vectors used for the transient expression of the CKα-4 protein gene sequence in mammalian cells should carry the SV40 origin of replication. This allows the replication of the vector to high copy numbers in cells (e.g., COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLV-I, HIV-I and the early promoter of the cytomegalovirus (CMV). However, cellular signals can also be used (e.g., human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 283, H9 and Jurkart cells, mouse NIH3T3 and C127 cells, Cos 1, Cos 7 and CV1, African green monkey cells, quail QC1-3 cells, mouse L cells and Chinese hamster ovary cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Another useful selection marker is the enzyme glutamine synthase (GS) (Murphy et al., Biochem J. 227:277–279 (1991); Bebbington et al., Bio/Technology 10:169–175 (1992)). Using these markers, the mammalian cells are grown in selective medium and the cells with the highest resistance are selected. These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., Molecular and Cellular Biology, 438–447 (March, 1985)) plus a fragment of the CMV-enhancer (Boshart et al., Cell 41:521–530 (1985)). Multiple cloning sites, e.g., the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pCKα-4 HA, is made by cloning a cDNA encoding CKα-4 into the expression vector pcDNAI/Amp (which can be obtained from Invitrogen, Inc.).

The expression vector pcDNAIHA/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polylinker, 50 an HA tag fused in frame to the 3' end of the gene.

A DNA fragment encoding the CKα-4 protein is cloned into the polylinker region of the vector so that recombinant protein expression is directed by the CMV promoter. The HA tag corresponds to an epitope derived from the influenza hemagglutinin protein described by Wilson et al., Cell 37: 767 (1984). The fusion of the HA tag to the target protein allows easy detection of the recombinant protein with an antibody that recognizes the HA epitope.

The plasmid construction strategy is as follows. The CKα-4 cDNA of the deposited clone is amplified using primers that contain convenient restriction sites, much as described above regarding the construction of expression vectors for expression of CKα-4 in *E. coli*. To facilitate detection, purification and characterization of the expressed CKα-4, the vector contains an HA tag fused in frame to its 3' end, as described above.

Suitable primers include the following, which are used in this example. The 5' primer, containing the underlined BamHI site, has the following sequence:

5'gactggatccgccatcatgagtgtgaagggcatgg 3' (SEQ D NO:6).

The 3'primer, containing the underlined XhoI site, has the following sequence:

5'cagctcgagaaaattctctttcaacttt 3' (SEQ ID NO:8).

The PCR amplified DNA fragment is digested with BamHI and XhoI and the vector, pcDNAI/Amp, is digested with BamHI. The digested fragment and vector are then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis and gel sizing for the presence of the CKα-4-encoding fragment.

For expression of recombinant CKα-4, COS cells are transfected with an expression vector, as described above, using DEAE-DEXTRAN, as described, for instance, in Sambrook et al., Molecular Cloning: a Laboratory Manual, Cold Spring Laboratory Press, Cold Spring Harbor, N.Y. (1989). Cells are incubated under conditions for expression of CKα-4 by the vector.

Expression of the CKα-4 HA fusion protein is detected by radiolabelling and lmmunoprecipitation, using methods described in, for example Harlow et al., Antibodies: A Laboratory Manual, 2nd Ed.; Cold Spring Harbor Laboratory Press, Cold Spring Harbor, N.Y. (1988). To this end, two days after transfection, the cells are labeled by incubation-in media containing 35S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

Example 3(b)

Cloning and Expression in CHO Cells

The vector pC4 is used for the expression of CKα-4 protein. Plasmid pC4 is a derivative of the plasmid pSV2-dhfr [ATCC Accession No. 37146]. Both plasmids contain the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Tedhnologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, J. Biol. Chem. 253:1357–1370, Hamlin, J. L. and Ma, C. 1990, Biochem. et Biophys. Acta, 1097:107–143, Page, M. J. and Sydenham, M. A. 1991, Biotechnology 9:64–68). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC4 contains for the expression of the gene of interest a strong promoter of the long terminal repeat (LTR) of the Rouse Sarcoma Virus (Cullen, et al., Molecular and Cellular Biology, March 1985:438–4470) plus a fragment isolated from the enhancer of the immediate early gene of human cytomegalovirus (CMV) (Boshart et al., Cell 41:521–530, 1985). Downstream of the promoter are the following single restriction enzyme cleavage sites that allow the integration of the genes: BamHI, XbaI and Asp718, followed by the 3' intron and the polyadenylation site of the rat preproinsulin gene. Other high efficient promoters can also be used for the expression, e.g., the human β-actin promoter, the SV40 early or late promoters or the long terminal repeats from other retroviruses, e.g., HIV and HTLV-I. For the polyadenylation of the mRNA other signals, e.g., from the human growth hormone or globin genes can be used as well.

Stable cell lines carrying a gene of interest integrated into the chromosomes can also be selected upon co-transfection with a selectable marker such as gpt, GST, G418 or hygromycin. It is advantageous to use more than one selectable marker in the beginning, e.g., G418 plus methotrexate.

The plasmid pC4 is digested with the restriction enzymes BamHI and Asp718 and then dephosphorylated using calf intestinal phosphatase by procedures known in the art. The vector is then isolated from a 1% agarose gel.

The DNA sequence encoding CKα-4, ATCC 97692 is amplified using the following PCR oligonucleotide primers:

The 5' primer has the sequence 5' gactggatccgccatcatgagtgtgaagggcatgg 3' (SEQ ID NO:6) containing the underlined BamHI restriction enzyme site. Inserted into an expression vector, as described below, the 5' end of the amplified fragment encoding human CKα-4 provides an efficient signal for initiation of translation in eukaryotic cells, as described by Kozak, M., J. Mol. Biol. 196:947–950 (1987).

The 3' primer has the sequence 5' gactggatcccagatgctcttttccaggac 3' (SEQ ID NO:7) containing the BamHI restriction site.

The amplified fragments are isolated from a 1% agarose gel as described above and then digested with the endonuclease BamHI and then purified again on a 1% agarose gel.

The isolated fragment and the dephosphorylated vector are then ligated with T4 DNA ligase. *E. coli* HB101 cells are then transformed and bacteria identified that contained the plasmid pC4 inserted in the correct orientation using the restriction enzyme BamHI. The sequence of the inserted gene is confirmed by DNA sequencing.

Transfection of CHO-DHFR-cells

Chinese hamster ovary cells lacking an active DHFR enzyme are used for transfection. 5 μg of the expression plasmid C4 are cotransfected with 0.5 μg of the plasmid pSV2-neo using the lipofecting method (Felgner et al., supra). The plasmid pSV2-neo contains a dominant selectable marker, the gene neo from Tn5 encoding an enzyme that confers resistance to a group of antibiotics including G418, which serves as a methotrexate resistance marker. The cells are seeded in alpha minus MEM supplemented with 1 mg/ml G418. After 2 days, the cells are trypsinized and seeded in hybridoma cloning plates (Greiner, Germany).

The cells are cultivated for 10–14 days in a- MEM media supplemented with 1 mg/ml G418 and using different concentrations of methotrexate (10 nM, 25 nM and 50 nM). After this period, single clones are trypsinized and then seeded in 6-well petri dishes using different concentrations of methotrexate (25 nM, 50 nM, 100 nM, 200 nM, 400 nM). Clones growing at the highest concentrations of methotrexate are then transferred to new 6-well plates containing even higher concentrations of methotrexate (500 nM, 1 μM, 2 μM, 5 μM). The same procedure is repeated until clones grow at a concentration of 100 μM.

The expression of the desired gene product is analyzed by Western blot analysis and SDS-PAGE.

Example 4

Tissue distribution of CKα-4 Protein Expression

Northern blot analysis is carried out to examine CKα-4 gene expression in human tissues, using methods described by, among others, Sambrook et al., cited above. A cDNA probe containing the entire nucleotide sequence of the CKα-4 protein (SEQ ID NO:1) is labeled with 32P using the rediprime™ DNA labeling system (Amersham Life Science), according to manufacturer's instructions. After labelling, the probe is purified using a CHROMA SPIN-100™ column (Clontech Laboratories, Inc., Palo Alto, Calif.), according to manufacturer's protocol number PT1200-1. The purified labelled probe is then used to examine various human tissues for CKα-4 mRNA.

Multiple Tissue Northern (MTN) blots containing various human tissues (H) or human immune system tissues (IM) are obtained from Clontech and are examined with the labelled probe using ExpressHyb™ hybridization solution (Clontech) according to manufacturer's protocol number PT1190-1. Following hybridization and washing, the blots are mounted and exposed to film at −70° C. overnight, and films developed according to standard procedures.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. An isolated cell that produces an antibody or fragment thereof, wherein said antibody or fragment thereof specifically binds to a peptide selected from the group consisting of:

(a) a peptide consisting of the amino acid sequence of amino acid residues 23 to 32 of SEQ ID NO:2;

(b) a peptide consisting of the amino acid sequence of amino acid residues 35 to 49 of SEQ ID NO:2;

(c) a peptide consisting of the amino acid sequence of amino acid residues 52 to 62 of SEQ ID NO:2; and (d) a peptide consisting of the amino acid sequence of amino acid residues 66 to 94 of SEQ ID NO:2.

2. A hybridoma that produces an antibody or fragment thereof, wherein said antibody or fragment thereof specifically binds to a peptide selected from the group consisting of:

(a) a peptide consisting of the amino acid sequence of amino acid residues 23 to 32 to 2 of SEQ ID NO:2;

(b) a peptide consisting of the amino acid sequence of amino acid residues 35 to 49 of SEQ ID NO:2;

(c) a peptide consisting of the amino acid sequence of amino acid residues 52 to 62 of SEQ ID NO:2; and (d) a peptide consisting of the amino acid sequence of amino acid residues 66 to 94 of SEQ ID NO:2.

3. An isolated monoclonal antibody or fragment thereof obtained from an animal that has been immunized with a peptide selected from the group consisting of:

(a) a peptide comprising the amino acid sequence of amino acid residues 23 to 32 of SEQ ID NO:2;

(b) a peptide comprising the amino acid sequence of amino acid residues 35 to 49 of SEQ ID NO:2;

(c) a peptide comprising the amino acid sequence of amino acid residues 52 to 62 of SEQ ID NO:2; and (d) a peptide comprising the amino acid sequence of amino acid residues 66 to 94 of SEQ ID NO:2;

wherein said antibody or fragment thereof specifically binds to said amino acid sequence.

4. An isolated cell that produces a monoclonal antibody or fragment thereof that specifically binds to a peptide selected from the group consisting of:

(a) a peptide consisting of amino acid residues 23 to 32 of SEQ ID NO:2;

(b) a peptide consisting of amino acid residues 35 to 49 of SEQ ID NO:2;

(c) a peptide consisting of amino acid residues 35 to 62 of SEQ ID NO:2;

(c) a peptide consisting of amino acid residues 52 to 62 of SEQ ID NO:2; and (d) a peptide consisting of amino acid residues 66 to 94 of SEQ ID NO:2.

5. A hybridoma that produces a monoclonal antibody or fragment thereof that specifically binds to a peptide selected from the group consisting of:

(a) a peptide consisting of amino acid residues 23 to 32 of SEQ ID NO:2;

(b) a peptide consisting of amino acid residues 35 to 49 of SEQ ID NO:2;

(c) a peptide consisting of amino acid residues 52 to 62 of SEQ ID NO:2; and (d) a peptide consisting of amino acid residues 66 to 94 of SEQ ID NO:2.

6. The isolated cell of claim 1, wherein said antibody or fragment thereof specifically binds peptide (a).

7. The isolated cell of claim 1, wherein said antibody or fragment thereof specifically binds peptide (b).

8. The isolated cell of claim 1, wherein said antibody or fragment thereof specifically binds peptide (c).

9. The isolated cell of claim 1, wherein said antibody or fragment thereof specifically binds peptide (d).

10. The hybridoma of claim wherein said antibody or fragment thereof specifically binds peptide (a).

11. The hybridoma of claim 2, wherein said antibody or fragment thereof specifically binds peptide (b).

12. The hybridoma of claim 2, wherein said antibody or fragment thereof specifically binds peptide (c).

13. The hybridoma of claim 3, wherein said antibody or fragment thereof specifically binds peptide (d).

14. The monoclonal antibody or fragment thereof of claim 3 obtained from an animal immunized with peptide (a).

15. The monoclonal antibody or fragment thereof of claim 3 obtained from an animal immunized with peptide (b).

16. The monoclonal antibody or fragment thereof of claim 3 obtained from an animal immunized with peptide (c).

17. The monoclonal antibody or fragment thereof of claim 3 obtained from an animal immunized with peptide (d).

18. The monoclonal antibody or fragment thereof of claim 3, wherein said peptide specifically bound by said monoclonal antibody or fragment thereof is glycosylated.

19. The monoclonal antibody or fragment thereof of claim 3, which is a chimeric antibody.

20. The isolated cell of claim 4, wherein said monoclonal antibody or fragment thereof specifically binds peptide (a).

21. The isolated cell of claim 4, wherein said monoclonal antibody or fragment thereof specifically binds peptide (b).

22. The isolated cell of claim 4, wherein said monoclonal antibody or fragment thereof specifically binds peptide (c).

23. The isolated cell of claim 4, wherein said monoclonal antibody or fragment thereof specifically binds peptide (d).

24. The hybridoma of claim 5, wherein said monoclonal antibody or fragment thereof specifically binds peptide (a).

25. The hybridoma of claim 5, wherein said monoclonal antibody or fragment thereof specifically binds peptide (b).

26. The hybridoma of claim 5, wherein said monoclonal antibody or fragment thereof specifically binds peptide (c).

27. The hybridoma of claim 5, wherein said monoclonal antibody or fragment thereof specifically binds peptide (d).

* * * * *

UNITED STATES PATENT AND TRADEMARK OFFICE

CERTIFICATE OF CORRECTION

PATENT NO. : 6,576,445 B1
APPLICATION NO. : 09/630709
DATED : June 10, 2003
INVENTOR(S) : Olsen et al.

It is certified that error appears in the above-identified patent and that said Letters Patent is hereby corrected as shown below:

Col. 52, In Claim 10, insert -- 2 -- after the word "claim"

Signed and Sealed this

Eighth Day of August, 2006

JON W. DUDAS
*Director of the United States Patent and Trademark Office*

SEQUENCE LISTING

```
(1) GENERAL INFORMATION:

   (iii) NUMBER OF SEQUENCES: 12


(2) INFORMATION FOR SEQ ID NO: 1:

     (i) SEQUENCE CHARACTERISTICS:
          (A) LENGTH: 686 base pairs
          (B) TYPE: nucleic acid
          (C) STRANDEDNESS: single
          (D) TOPOLOGY: linear

    (ii) MOLECULE TYPE: DNA (genomic)

    (ix) FEATURE:
          (A) NAME/KEY: CDS
          (B) LOCATION: 66..347

    (xi) SEQUENCE DESCRIPTION: SEQ ID NO: 1:

AGCCAAGAAG AGCAGCAAAG CTGAAGTAGC AGCAGCAGCA CCAGCAGCAA CAGCAAAAAA      60

CAAAC ATG AGT GTG AAG GGC ATG GCT ATA GCC TTG GCT GTG ATA TTG        107
      Met Ser Val Lys Gly Met Ala Ile Ala Leu Ala Val Ile Leu
        1               5                  10

TGT GCT ACA GTT GTT CAA GGC TTC CCC ATG TTC AAA AGA GGA CGC TGT      155
Cys Ala Thr Val Val Gln Gly Phe Pro Met Phe Lys Arg Gly Arg Cys
 15                  20                  25                  30

CTT TGC ATA GGC CCT GGG GTA AAA GCA GTG AAA GTG GCA GAT ATT GAG      203
Leu Cys Ile Gly Pro Gly Val Lys Ala Val Lys Val Ala Asp Ile Glu
                 35                  40                  45

AAA GCC TCC ATA ATG TAC CCA AGT AAC AAC TGT GAC AAA ATA GAA GTG      251
Lys Ala Ser Ile Met Tyr Pro Ser Asn Asn Cys Asp Lys Ile Glu Val
             50                  55                  60

ATT ATT ACC CTG AAA GAA AAT AAA GGA CAA CGA TGC CTA AAT CCC AAA      299
Ile Ile Thr Leu Lys Glu Asn Lys Gly Gln Arg Cys Leu Asn Pro Lys
         65                  70                  75
```

-continued

```
TCG AAG CAA GCA AGG CTT ATA ATC AAA AAA GTT GAA AGA AAG AAT TTT      347
Ser Lys Gln Ala Arg Leu Ile Ile Lys Lys Val Glu Arg Lys Asn Phe
     80                  85                  90

TAAAAATATC AAAACATATG AAGTCCTGGA AAAGAGCATC TGAAAAACCT AGAACAAGTT    407

TAACTGTGAC TACTGAAATG ACAAGAATTC TACAGTAGGA AACTGAGACT TTTCTATGGT    467

TTTGTGACTT TCAACTTTTG TACAGTTATG TGAAGGATGA AAGGTGGGTG AAAGGACCAA    527

AAACAGAAAT ACAGTCTTCC TGAATGAATG ACAATCAGAA TTCCACTGCC CAAAGGAGTC    587

CAACAATTAA ATGGATTTCT AGGAAAAGCT ACCTTAAGAA AAGGGCTGGT TACCATCGGA    647

GTTTACAAAG TGCTTTCACG TTCTTACTTG TTGCATTAT                           686
```

(2) INFORMATION FOR SEQ ID NO: 2:

(i) SEQUENCE CHARACTERISTICS:
(A) LENGTH: 94 amino acids
(B) TYPE: amino acid
(D) TOPOLOGY: linear (ii) MOLECULE TYPE: protein (xi) SEQUENCE DESCRIPTION: SEQ ID NO: 2:

```
Met Ser Val Lys Gly Met Ala Ile Ala Leu Ala Val Ile Leu Cys Ala
  1               5                  10                  15

Thr Val Val Gln Gly Phe Pro Met Phe Lys Arg Gly Arg Cys Leu Cys
             20                  25                  30

Ile Gly Pro Gly Val Lys Ala Val Lys Val Ala Asp Ile Glu Lys Ala
        35                  40                  45

Ser Ile Met Tyr Pro Ser Asn Asn Cys Asp Lys Ile Glu Val Ile Ile
     50                  55                  60

Thr Leu Lys Glu Asn Lys Gly Gln Arg Cys Leu Asn Pro Lys Ser Lys
 65                  70                  75                  80

Gln Ala Arg Leu Ile Ile Lys Lys Val Glu Arg Lys Asn Phe
                 85                  90
```

(2) INFORMATION FOR SEQ ID NO: 3:

(i) SEQUENCE CHARACTERISTICS:
(A) LENGTH: 92 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 3:

```
Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
    50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu
                85                  90
```

-continued (2) INFORMATION FOR SEQ ID NO: 4:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 4:

GACTCATGAC AGTTGTTCAA GGCTCC 26

(2) INFORMATION FOR SEQ ID NO: 5:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 5:

GACAGATCTT TAAAAATTCT TTCTTTCAAC TT 32

(2) INFORMATION FOR SEQ ID NO: 6:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 6:

GACTGGATCC GCCATCATGA GTGTGAAGGG CATGG 35

(2) INFORMATION FOR SEQ ID NO: 7:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 7:

GACTGGTACC CAGATGCTCT TTTCCAGGAC 30

(2) INFORMATION FOR SEQ ID NO: 8:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 8:

CAGCTCGAGA AAATTCTTTC TTTCAACTTT 30

-continued (2) INFORMATION FOR SEQ ID NO: 9:

(i) SEQUENCE CHARACTERISTICS:
(A) LENGTH: 377 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 9:

```
CAAAGCTGAA GTAGCAGCAA CAGCACCAGC AGCAACAGCA AAAAACAAAC ATGAGTGTGA     60

AGGGCATGGC TATAGCCTTG GCTGTGATAT TGTGTGCTAC AGTTGTTCAA GGTATGCAGT    120

AATTTTNATT TCTCAACCTA TAAGTTCCTN TTCTAATGTT TCAAATGTCT TTTCTTCCAC    180

TTTTATCCTA AAAGACATGA TAAAGTTTTA TTTAATCTCA CAGATTAGAA GTTACTACAG    240

CTTTAGCACA GAAATGGTGG NCATGTTTAA GATACTAGAG ATGATTATTG AANCTAGAAA    300

TTATGGACTT CATGGAATTT TTNGGATTTG GCTAGAATTA TCTGGCAAAA GNCTTTTAGG    360

CAACCAGTTT TAAATGT                                                   377
```

(2) INFORMATION FOR SEQ ID NO: 10:

(i) SEQUENCE CHARACTERISTICS:
(A) LENGTH: 112 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 10:

```
CAAAGCTGAA GTAGCAGCAA CAGCACCAGC AGCAACAGCA AAAAACAAAC ATGAGTGTGA     60

AGGGCATGGC TATAGCCTTG GCTGTGATAT TGTGTGCTAC AGTTGTTCAA GG            112
```

(2) INFORMATION FOR SEQ ID NO: 11:

(i) SEQUENCE CHARACTERISTICS:
(A) LENGTH: 301 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 11:

```
ACGATGCCTA AATCCCAAAT CGAAGCAAGC AAGGCTTATA ATCAAAAAAG TTGAAAGAAA     60

GATTTTTAAA AAATATCAAA ACATATGAGT CCTGGAAAAG GGCATCTGAA AAACCTAGAA    120

CAAGTTTAAC TGTGACTACT GAAATGACAA GAATTCTACA GTAGGAAACT GAGACTTTTC    180

TATGGTTTTT GACTTTCAAC TTTTGTACAG TTATGTGAAG GATGAAAGGT GGGTGAAAGG    240

ACCAAAAACA GAAATACAGT CTTCCTGAAT GATTGACAAT CCAGATTCCA CTGCCCAAAG    300

G                                                                    301
```

(2) INFORMATION FOR SEQ ID NO: 12:

(i) SEQUENCE CHARACTERISTICS:
(A) LENGTH: 305 base pairs
(B) TYPE: nucleic acid
(C) STRANDEDNESS: single
(D) TOPOLOGY: linear (ii) MOLECULE TYPE: DNA (genomic)

-continued (xi) SEQUENCE DESCRIPTION: SEQ ID NO: 12:

```
ACGATGCCTA AATCCCAAAT CGAAGCAAGC AAGGCTTATA ATCAAAAAAG TTGAAAGAAA     60

GANTTTTTAA AAAATATCAA AACATATGAN GTCCTGGAAA AGGGCATCTG AAAAACCTAG    120

AACAAGTTTA ACTGTGACTA CTGAAATGAC AAGAATTCTA CAGTAGGAAA CTGAGACTTT    180

TCTATGGTTT TNTGACTTTC AACTTTTGTA CAGTTATGTG AAGGATGAAA GGTGGGTGAA    240

AGGACCAAAA ACAGAAATAC AGTCTTCCTG AATGATTGAC AATCCAGANT TCCACTGCCC    300

AAAGG                                                                305
```